United States Patent
Okamoto

(10) Patent No.: US 9,055,894 B2
(45) Date of Patent: Jun. 16, 2015

(54) EYE REFRACTIVE POWER MEASURING APPARATUS AND CALIBRATION METHOD OF EYE REFRACTIVE POWER MEASURING APPARATUS

(71) Applicant: TOMEY CORPORATION, Nagoya-shi (JP)

(72) Inventor: Keiichiro Okamoto, Nagoya (JP)

(73) Assignee: TOMEY CORPORATION (JP)

( * ) Notice: Subject to any disclaimer, the term of this patent is extended or adjusted under 35 U.S.C. 154(b) by 15 days.

(21) Appl. No.: 14/096,130

(22) Filed: Dec. 4, 2013

(65) Prior Publication Data

US 2014/0152958 A1   Jun. 5, 2014

(30) Foreign Application Priority Data

Dec. 4, 2012   (JP) ................. 2012-265202

(51) Int. Cl.
- A61B 3/10 (2006.01)
- A61B 3/14 (2006.01)
- A61B 3/103 (2006.01)

(52) U.S. Cl.
CPC ............... A61B 3/103 (2013.01); A61B 3/1035 (2013.01)

(58) Field of Classification Search
USPC .................................. 351/200–246
See application file for complete search history.

(56) References Cited

U.S. PATENT DOCUMENTS

| | | | |
|---|---|---|---|
| 6,695,450 B2* | 2/2004 | Hirohara et al. | 351/211 |
| 7,416,301 B2 | 8/2008 | Hanebuchi et al. | 351/205 |
| 2013/0242258 A1* | 9/2013 | Higuchi | 351/206 |

FOREIGN PATENT DOCUMENTS

| | | |
|---|---|---|
| JP | 63-31633 | 2/1988 |
| JP | 2005-185523 | 7/2005 |

* cited by examiner

*Primary Examiner* — Mohammed Hasan
(74) *Attorney, Agent, or Firm* — Grossman Tucker Perreault & Pfleger PLLC

(57) ABSTRACT

An eye refractive power measuring apparatus includes a light projecting optical system, a light receiving optical system, a focusing unit, a calibration optical system, a focus control unit, and an arithmetic unit. The arithmetic unit, based on a relation of a control signal obtained when a calibration beam is projected and a calibration value that is an output of a light receiving unit, and a correlation of a calibration value obtained in advance and eye refractive power, calculates a correlation of the control signal and the eye refractive power, and, based on a control signal obtained when measuring beam is projected, a measured value that is an output of the light receiving unit, and the correlation, calculates the eye refractive power.

10 Claims, 15 Drawing Sheets

EYE REFRACTIVE POWER MEASURING APPARATUS AND CALIBRATION METHOD OF EYE REFRACTIVE POWER MEASURING APPARATUS

CROSS-REFERENCE TO RELATED APPLICATIONS

This application claims the benefit of Japanese Patent Application No. 2012-265202 filed Dec. 4, 2012 in the Japan Patent Office, the disclosure of which is incorporated herein by reference.

BACKGROUND

The present invention relates to an eye refractive power measuring apparatus for measuring eye refractive power such as a spherical refractive power, an astigmatic power, and an astigmatism angle of a subject's eye, and a calibration method of an eye refractive power measuring apparatus.

As a method for measuring eye refractive power power for refracting light) of a subject's eye, a method has been known in which a target beam used for measurement is projected onto a fundus of the subject's eye, and an eye refractive power is measured based on the size, etc. of an image formed when light reflected on the fundus is imaged. Furthermore, an eye refractive power measuring apparatus that measures eye refractive power automatically based on this method (automatic refractometer has been known.

In such eye refractive power measuring apparatus, an eye refractive power measuring apparatus is known which, for the purpose of improving measurement accuracy of eye refractive power, includes a mechanism for moving a lens or a light receiving element. For example, in an eye refractive power measuring apparatus according to Japanese Patent Application Publication No. 2005-185523 (hereinafter, Patent Document 1), by moving a lens, etc. by a moving mechanism in accordance with an eye refractive power of a subject's eye, a target beam projected onto a fundus is focused. Therefore, it is possible to reduce measurement errors due to defocusing of the target beam.

In the eye refractive power measuring apparatus of Patent Document 1, in order to reduce the measurement errors in the eye refractive power, it is desirable that the lens, etc. is moved so that an optical axis of the lens matches an optical axis of an optical system. However, keeping the matching of the optical axes upon moving is difficult. There has been a problem that lowering of measurement accuracy due to misalignment of the optical axes is likely to occur.

To address the above problem, instead of providing a moving mechanism for moving the lens, etc. as described above, an eye refractive power measuring apparatus with a reduced movable mechanical portion is known in which a variable focus lens made of transparent silicone rubber or the like is arranged at a position conjugate with a pupil. For example, in the eye refractive power measuring apparatus of Japanese Patent Application Publication No. 63-031633 (hereinafter, Patent Document 2), in a state in which the position of the lens, etc. is fixed, the target beam projected onto the fundus is focused by moving a focal position of the lens, etc. Therefore, misalignment of the optical axes by the movement of the lens, etc. as above can be suppressed. Deterioration of measurement accuracy can be thus suppressed. Further, because a moving mechanism for moving the lens, etc. is not required, a configuration of the apparatus can be simplified. The apparatus itself can be downsized.

SUMMARY

In the eye refractive power measuring apparatus of Patent Document 1, in addition to the problem that measurement errors of the eye refractive power could occur by moving the lens, etc. as described above, the following problems may occur. More specifically, in a sliding portion of the moving mechanism, wear caused by years of use and thereby misalignment of the position of the lens, etc. can occur. Then, measurement errors due to the misalignment can occur. Alternatively, measurement errors due to aging of an optical element such as a lens may occur. In addition, since it is necessary to employ a high accuracy guide mechanism or a more precise movement control in order to reduce misalignment of the optical axis at the time of moving the lens, etc., manufacturing costs can be high. Furthermore, since it is necessary to provide a moving mechanism, downsizing of the eye refractive power measuring apparatus is difficult.

As shown in FIG. 15, a variable focus lens provided in a eye refractive power measuring apparatus disclosed in Patent Document 2 has a characteristic in which refractive power changes, for example with temperature. Therefore, an eye refractive power value of a subject's eye obtained by the apparatus described in Patent Document 2 can include errors due to changes in ambient temperature.

One way to reduce errors due to changes in refractive power (in other words, changes in ambient temperature) of the variable focus lens is to provide a temperature control device that suppresses changes in temperature of the variable focus lens in the eye refractive power measuring apparatus. However, since a temperature control device is complex in its configuration, manufacturing costs thereof can be high. Furthermore, providing a temperature control device increases the size of the eye refractive power measuring apparatus.

It is desirable to provide an eye refractive power measuring apparatus which can achieve improved accuracy of measurements while suppressing an increase in size or manufacturing cost of the apparatus, and a calibration method of the eye refractive power measuring apparatus.

An eye refractive power measuring apparatus according to one aspect of the present invention includes a light projecting optical system, a light receiving optical system, a focusing unit, a calibration optical system, a focus control unit, and an arithmetic unit. The light projecting optical system projects a measuring beam for use in measurement of eye refractive power on a fundus of a subject's eye. The light receiving optical system causes a light receiving unit to receive reflected light from the fundus. The focusing unit forms an image of the reflected light on the light receiving unit by moving a focal position. The calibration optical system projects a calibration beam for use at least in calibration of the focusing unit. The focus control unit outputs to the focusing unit a control signal for controlling movement of the focal position. The arithmetic unit, based on a relation of the control signal obtained when the calibration beam is projected and a calibration value which is an output of the light receiving unit, and a correspondence relation of the calibration value and the eye refractive power obtained in advance, calculates a correlation of the control signal and the eye refractive power, and, based on the control signal obtained when the measuring beam is projected, a measured value, which is an output of the light receiving unit, and the correlation, calculates the eye refractive power.

According to the eye refractive power measuring apparatus according to one aspect of the present invention, by using the calibration beam instead of the measuring beam and causing the light receiving unit to artificially receive the calibration beam as the reflected light from the fundus, the correlation of the control signal input to the focusing unit and the eye refractive power in case of using the calibration beam is obtained. Then, based on the control signal when the measuring beam is projected, a measured value of the light receiving unit, and the acquired correlation, the eye refractive power of the subject's eye is calculated. By using the correlation obtained using the calibration beam as such, it is possible to reduce errors in the refractive power of the subject's eye to be calculated.

More specifically, changes in characteristics such as refractive power due to a temperature change and a change over time at least in the focusing unit, and changes of the measured value of the light receiving unit due to misalignment or the like of a position of lenses, etc. constituting the focusing unit, are reflected on the correlation obtained using the calibration beam. By correcting the eye refractive power of the subject's eye measured using the measuring beam based on the correlation, it is possible to reduce errors that can be included in the eye refractive power.

Further, the calibration optical system according to the present invention in one aspect, as compared with the case of using a temperature control device in order to reduce errors due to a temperature change in the focusing unit, requires a small space for disposition, and can be disposed in the eye refractive power measuring apparatus at a low price.

Further, in the focusing unit, misalignment in position of the lens, etc. occurs and an error occurs by moving the lens, etc. before and after the movement of the lens. The calibration optical system according to one aspect of the present invention can suppress errors caused by misalignment in position, by means of the correlation.

It is preferable that the focusing unit is a variable focus lens of which focal position moves as refractive power changes in response to the input control signal.

By using a variable focus lens as the focusing unit, as compared with the case of moving the focal position by moving the lens, it becomes easy to suppress errors that can be included in the eye refractive power to be calculated. In the case of configuration of moving the lens, etc., it is necessary to employ a moving mechanism that prevents misalignment by the movement between an optical axis of the lens and an optical axis of the light receiving optical system. On the other hand, when using a variable focus lens as the focusing unit, it is possible to move the focal position without moving the position of the lens. Therefore, misalignment of the optical axis due to the movement of the lens does not occur. It becomes easier to suppress errors due to the misalignment.

It is preferable that the variable focus lens is provided in the light receiving optical system, and moves at least the focal position of the reflected light imaged on the light receiving unit.

By providing a variable focus lens in the light receiving optical system, at least the focal position of the reflected light imaged on the light receiving unit is controlled by the variable focus lens. Therefore, as compared with the case of controlling the focal position of the reflected light by movement of the position of the lens, it is possible to remove an influence of misalignment of the optical axis due to the movement of the lens on the image on the light receiving unit. In other words, it becomes easier to suppress errors that can be included in the eye refractive power to be calculated.

It is preferable that a variable focus lens is provided in each of an area in the light receiving optical system independent of the light projecting optical system, and an area in the light projecting optical system independent of the light receiving optical system. The variable focus lens provided in the light receiving optical system moves the focal position of the reflected light imaged on said light receiving unit. The variable focus lens provided in the light projecting optical system moves the focal position of the measuring beam projected on the fundus.

By providing the variable focus lens in the light projecting optical system separately from the light receiving optical system in this manner, it is possible to prevent stray light generated by the measuring beam reflected by the variable focus lens from entering a light receiving element.

It is preferable that the variable focus lens is provided in an area common to the light receiving optical system and the light projecting optical system, moves the focal position of the reflected light imaged on the light receiving unit, and moves the focal position of the measuring beam projected on the fundus.

By providing a variable focus lens in an area common to the light receiving optical system and the light projecting optical system, it is possible to move the focal position of the reflected light and the focal position of the measuring beam by one variable focus lens. Therefore, it is possible, as compared with the case of separately providing a variable focus lens to move the focal position of the reflected light and a variable focus lens to move the focal position of the measuring beam, to reduce the number of variable focus lenses to be used, and to easily achieve downsizing and reduction in manufacturing cost of the eye refractive power measuring apparatus.

It is preferable that a fogging optical system that presents a fixation target to the subject's eye is further provided, and the fogging optical system separately has the variable focus lens. The variable focus lens provided in the fogging optical system is controlled based on the control signal output by the focus control unit based on the correlation.

By providing a variable focus lens in the fogging optical system and controlling the variable focus lens based on the correlation, it is easy to place the subject's eye in a fogging state, as compared with the case of not using a variable focus lens, or the case not based on the correlation. The fogging state is a state of the subject's eye in which accommodation power by the crystalline lens, etc. is not working, or in which influence on measurement of the eye refractive power is small even if accommodation power is working.

It is preferable that the variable focus lens is arranged at a position substantially conjugate with a pupil of the subject's eye. By arranging a variable focal lens at a position substantially conjugate with a pupil of the subject's eye, it is possible to prevent the reflected light from being focused on the position of the variable focus lens. Therefore, the variable focus lens can move the focal position of the reflected light. Here, the position substantially conjugate with the pupil can be illustrated as a range of about ±50 mm around the conjugate position of the pupil in an emmetropia eye.

It is preferable that a light source that emits the calibration beam in the calibration optical system is arranged at a position substantially conjugate with the fundus of the subject's eye, which is emmetropia.

By arranging the light source that emits the calibration beam at a position substantially conjugate with the fundus of the subject's eye, it is possible to calculate the correlation that can remove more errors, which can be included in the eye refractive power to be calculated, in comparison with the case of the light source not at a position substantially conjugate with the fundus. That is, by using the calibration beam emitted from the light source disposed at a position substantially conjugate with the fundus, upon calculating the correlation, compared with the case of using the calibration beam emitted from a position not substantially conjugate, it is possible to calculate the correlation under conditions close to those of the case of measuring the reflected light from the fundus. As a result, it becomes further easier to suppress errors that can be included in the eye refractive power.

A calibration method of an eye refractive power measuring apparatus according to one aspect of the present invention includes an acquisition step of projecting the calibration beam to the light receiving unit, outputting a plurality of the control signals having the different focal positions from the focus control unit to the focusing unit, and acquiring a calibration value which is an output of the light receiving unit every time the control signal is output, an approximation step of calculating an approximation formula representing a relation of the control signal to the corresponding calibration value, a correlation step of calculating a correlation of the control signal and the corresponding refractive power based on a correspondence relation of the calibration value, and the eye refractive power obtained in advance, and the approximation formula calculated in the approximation step, and a calibration step of calculating the eye refractive power based on the control signal obtained when the measuring beam is projected, the measured value, which is an output of the light receiving unit, and the correlation.

According to the calibration method of one aspect of the present invention, the approximation formula representing the relation of the control signal input to the focusing unit using the calibration beam and the calibration value, which is the output of the light receiving unit, is calculated. Based on the approximation formula and the correspondence relation of the calibration value and the eye refractive power obtained in advance, the correlation of the eye refractive power and the corresponding control signal is obtained. Based on this correlation, the control signal when the measuring beam is projected, and the measured value of the light receiving unit, the eye refractive power of the subject's eye is calculated. As compared with the case of not using the correlation, it is possible to reduce errors in the refractive power of the subject's eye to be calculated.

In the acquisition step, it is preferable that the control signals having the different focal positions output from the focus control unit include at least a signal of the focal position corresponding to the case where the subject's eye is shortsighted, and a signal of the focal position corresponding to the case where the subject's eye is hyperopic.

By calculating the correlation using at least the control signal of the focal position corresponding to the case where the subject's eye is shortsighted and the control signal of the focal position corresponding to the case where the subject's eye is hyperopic, errors that can be included in the eye refractive power to be calculated can be further suppressed.

According to the eye refractive power measuring apparatus according to one aspect of the present invention and the calibration method of the eye refractive power measuring apparatus according to one aspect, the correlation of the control signal input to the focusing unit using a calibration beam and the eye refractive power is obtained and the eye refractive power of the subject's eye is calculated based on the control signal when the measuring beam is projected, the measured value of the light receiving unit, and the obtained correlation. Thus, it is possible to achieve improved accuracy of measurements while an increase in size and manufacturing cost of the apparatus is suppressed.

BRIEF DESCRIPTION OF THE DRAWINGS

Hereinafter, with reference to the accompanying drawings, the present invention will be described as an example.

DETAILED DESCRIPTION OF THE PREFERRED EMBODIMENTS

First Embodiment

Hereinafter, an eye refractive power measuring apparatus 1 (hereinafter, apparatus 1) according to a first embodiment of the present invention will be described with reference to FIGS. 1-9D. The apparatus 1 according to the first embodiment is an apparatus for measuring eye refractive power of a subject's eye 90, which may be also used to select a refractive power of a spectacle lens used in eyeglasses for correcting visual acuity of the subject's eye 90.

Figure 1:
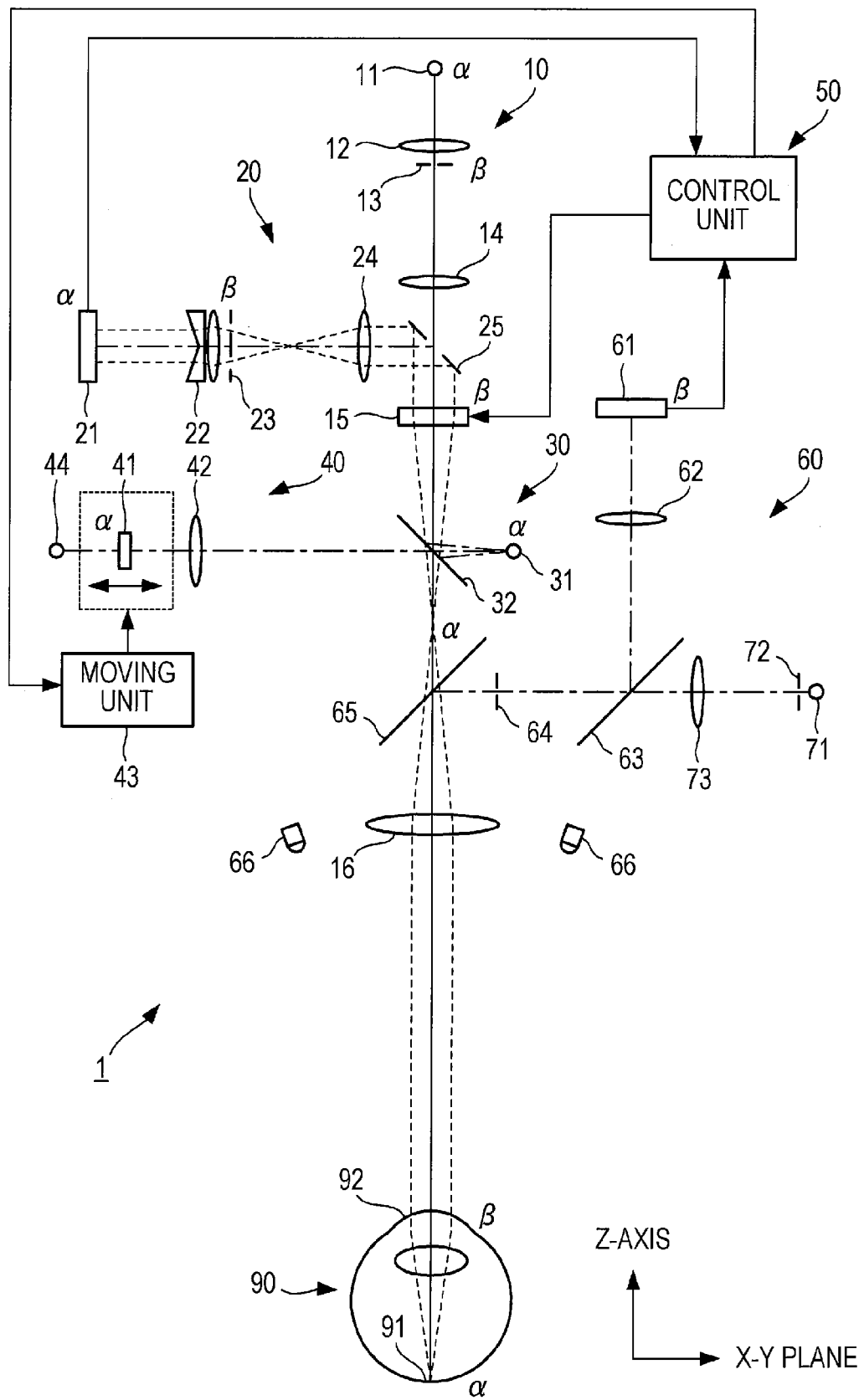
FIG. 1 is a schematic diagram illustrating an eye refractive power measuring apparatus according to a first embodiment of the present invention.
Figure 2:
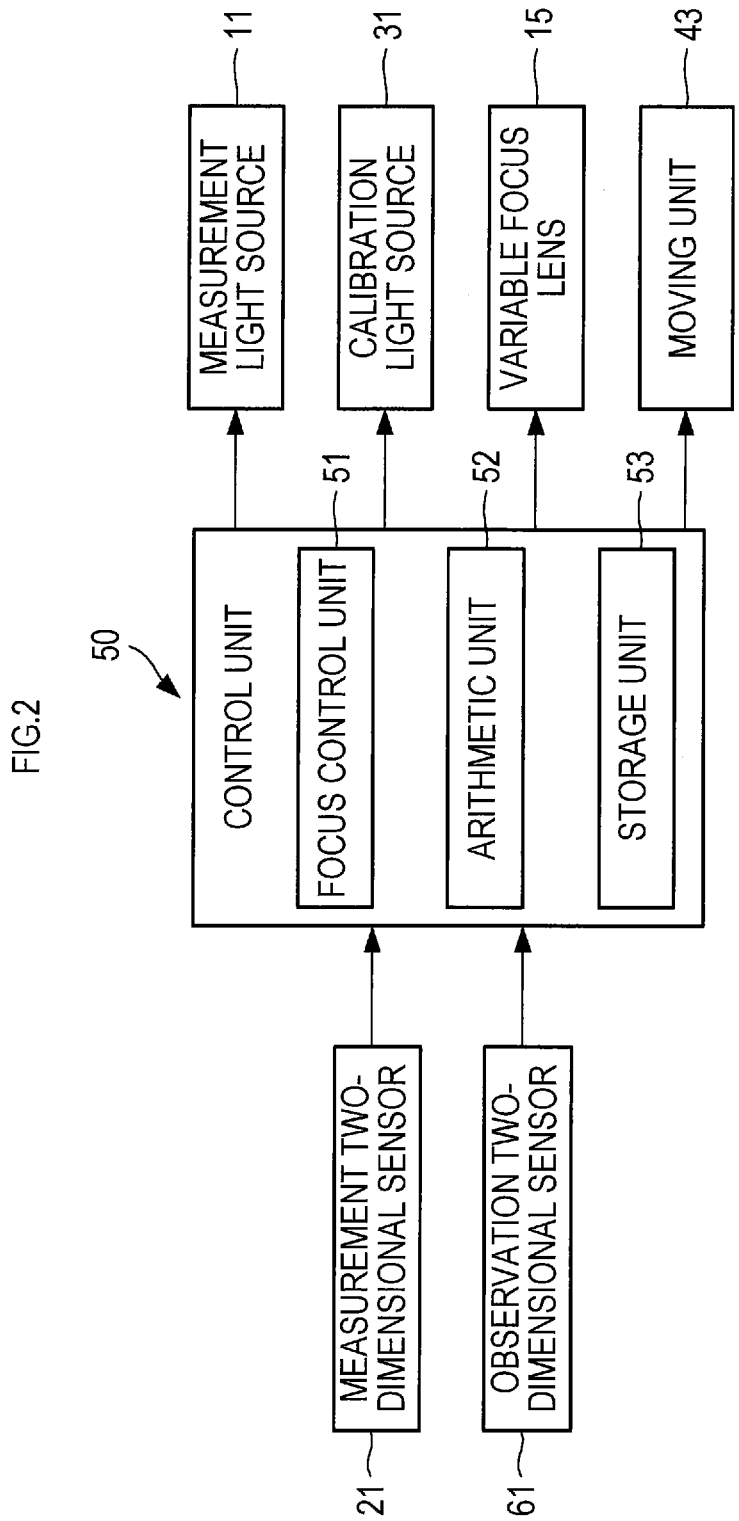
FIG. 2 is a block diagram illustrating a configuration of a control unit of FIG. 1.

The apparatus 1, as shown in FIG. 1, includes a light projecting optical system 10, a light receiving optical system 20, a calibration optical system 30, a fogging optical system 40, and a control unit 50. The apparatus further includes an anterior segment observation system 60. In the description of the first embodiment, a Z-axis is a straight line (optical axis) connecting a measurement light source 11 of the light projecting optical system 10 and the subject's eye 90, and an X-Y plane is a plane perpendicular to the Z axis.

The light projecting optical system 10 projects a measuring beam used for measurement of eye refractive power toward a fundus 91 of the subject's eye 90. The light projecting optical system 10 includes the measurement light source 11 (hereinafter, the light source 11), a first measuring relay lens 12 (hereinafter, the lens 12), a measurement diaphragm aperture 13 (hereinafter, the diaphragm 13), a second measuring relay lens 14 (hereinafter, the lens 14), a variable focus lens (an example of the focusing unit) 15 (hereinafter, the lens 15) that is shared with the light receiving optical system 20, and an objective lens 16. The light source 11, the lens 12, the diaphragm 13, the lens 14, the lens 15, and the objective lens 16 are arranged in the order described above on an optical axis of the light projecting optical system 10.

The light source 11 emits the measuring beam. The light source 11 may emit an infrared ray having a wavelength (λ) of 800 nm. The light source 11 is positioned substantially conjugate with the fundus 91 of the subject's eye 90 (position indicated by (α) in the figure).

The lens 12 and the lens 14 are convex lenses that lead the measuring beam emitted from the light source 11 to the lens 15. The diaphragm 13 has a through hole (not shown) that narrows and passes the measuring beam. The through hole is provided to match the optical axis. When the measuring beam passes through the through hole, the measuring beam becomes a light beam along the optical axis. The diaphragm 13 is positioned between the lens 12 and lens 14 and is substantially conjugate with a pupil 92 of the subject's eye 90 (the position indicated by (β) in the figure).

The lens 15 and the objective lens 16 are used in common with the light projecting optical system 10 and the light receiving optical system 20 as described above. In the light projecting optical system 10, by lens 15 and the objective lens 16, the measuring beam is focused on the fundus 91. The lens 15 is positioned substantially conjugate with the pupil 92 of the subject's eye 90 (the position indicated by (β) in the figure).

The lens 15 is a lens that can move a focal position by a control signal input from the control unit 50 without moving its position. The lens 15 may be a liquid lens (e.g., a liquid lens of Varioptic) that moves the focal position by controlling a boundary surface between oil and an aqueous solution sealed inside a module by an applied voltage. The lens 15 may be, but is not particularly limited to, a lens made from silicone rubber.

The light receiving optical system 20 causes a measurement two-dimensional sensor (an example of the light receiving unit) 21 (hereinafter, the sensor 21), which will be described later, to receive reflected light from the fundus 91. The light receiving optical system 20 includes the sensor 21, a first light receiving relay lens 22 (hereinafter, the lens 22), a ring diaphragm 23, a second light receiving relay lens 24 (hereinafter, the lens 24), a light receiving mirror 25 (hereinafter, the mirror 25), the lens 15 and the objective lens 16 that are shared with the light projecting optical system 10.

The sensor 21 is formed by arranging a plurality of light receiving elements, such as a CCD (charge coupled device) or a CMOS (Complementary Metal Oxide Semiconductor), in a planar manner. The measuring beam emitted to the fundus 91 is reflected on the fundus 91, and the reflected light is imaged on the sensor 21 and detected by the sensor 21. The sensor 21 is positioned substantially conjugate with the fundus 91 of the subject's eye 90 (the position indicated by (α) in the figure). A measurement signal (signal representing a result of detection of the imaged reflected light) by the sensor 21 is output to the control unit 50.

The lens 22 and lens 24 lead the reflected light reflected on the fundus 91 and transmitted through the lens 15 to the sensor 21. The lens 22 is a combination of a convex lens and a lens of which one surface is formed in a conical shape. The lens 24 is a convex lens.

The ring diaphragm 23 has a ring-shaped slit for narrowing and passing the reflected light (not shown). The ring diaphragm 23 is provided so that a center of the ring-shaped slit matches the optical axis of the light receiving optical system 20. The reflected light passing through the ring-shaped slit forms an annular (ring-shaped) image on the sensor 21. The ring diaphragm 23 is positioned between the lens 22 and lens 24 and is substantially conjugate with the pupil 92 of the subject's eye 90 (the position indicated by (β) in the figure).

The mirror 25 is disposed between the lens 24 and lens 15 in the light receiving optical system 20, and bends the optical axis of the light receiving optical system 20 (optical axis extending in the Z axis direction) in the X-Y plane direction. It may be understood that the mirror 25 is disposed on the optical axis of the light projecting optical system 10. More specifically, the mirror 25 is disposed between the lens 14 and lens 15 in the light projecting optical system 10. The mirror 25 has a through hole through which the measuring beam passes. The mirror 25 is disposed so that a center of the through hole matches the optical axis of the light projecting optical system 10.

The calibration optical system 30 projects a calibration beam used at least for calibration of the lens 15. The calibration optical system 30 includes a calibration light source (an example of the light source) 31 (hereinafter, the light source 31), and a reflective mirror 32 that is shared with the fogging optical system 40.

The light source 31 emits a calibration beam. The light source 31 may emit an infrared ray having a wavelength (λ) of about 800 nm, similar to the measuring beam. The light source 31 is positioned substantially conjugate with the fundus 91 of the subject's eye 90 (position indicated by (α) in the figure).

The reflective mirror 32 is disposed between the lens 15 and the objective lens 16, transmits the measuring beam emitted from the light source 11 and the reflected light reflected on the fundus 91, and reflects at least part of the calibration beam (1%, for example) emitted from the light source 31 toward the lens 15. In the fogging optical system 40 to be described later, a visible light from a visible light source 44 is irradiated on a fixation target 41, and the irradiated light is reflected on the reflective mirror 32 to reach the subject's eye 90. Thus, the fixation target 41 can be viewed by the subject's eye 90. As the reflective mirror 32, for example, a cold mirror may be employed.

The fogging optical system 40 is used to bring a state of the subject's eye 90 into a state in which accommodation power by a crystalline lens, etc. is not working, or a state in which influence on measurement of eye refractive power is small even if accommodation power is working. The fogging optical system 40 includes the visible light source 44, the fixation target 41, a fogging relay lens 42 (hereinafter, the lens 42), the reflective mirror 32 that is shared with the calibration optical system 30, and a moving unit 43.

On the fixation target 41, a predetermined figure or a pattern, etc. to be presented to the subject's eye 90 is depicted. The fixation target 41 is disposed in a position substantially conjugate with the fundus 91 of the subject's eye 90 (position indicated in (α) in the figure). The fixation target 41 and the lens 42 are arranged side by side on an optical axis of the fogging optical system 40 together with the reflective mirror 32.

The moving unit 43 is a drive mechanism that moves the fixation target 41 along the optical axis of the fogging optical system 40. The control signal from the control unit 50 is input to the moving unit 43. In accordance with the control signal, the moving unit 43 moves the position of the fixation target

41. A known linear drive mechanism in the art may be used for configuring the moving unit 43. Types of the drive mechanism are not particularly limited.

The control unit 50 includes a microcomputer having a CPU (central processing unit), a ROM, a RAM, and an input and output interface. The control unit 50 controls operation of the apparatus 1, and performs calculations required when calculating the eye refractive power of the subject's eye 90. A control program stored in the ROM, etc. causes the CPU to function as the focus control unit 51 and/or an arithmetic unit 52 in FIG. 2. The ROM or the RAM may correspond to an example of the storage unit 53. The control unit 50 performs various controls such as lighting control of the light source 11 and the light source 31, control of the moving unit 43, and alignment adjustment control.

The focus control unit 51 outputs to the lens 15 a control signal for controlling movement of the focal position. In the lens 15 used in the first embodiment, the focal position is controlled by an applied voltage. In this case, the control signal output from the focus control unit 51 may be an applied voltage. Based on the signal output from the CPU, the focus control unit 51 may control the control signal to the lens 15 (e.g., voltage to be applied to the lens 15).

The arithmetic unit 52 and the storage unit 53 calculate a relational expression (correlation) used when calculating the eye refractive power and performs calculations required when calculating the eye refractive power of the subject's eye 90. Details about arithmetic processes performed by the arithmetic unit 52 and the storage unit 53 will be described later.

The anterior segment observation system 60 is used for observation of an anterior segment including the pupil 92 of the subject's eye 90, and is also used for adjustment of the positions (alignment adjustment) of the light projecting optical system 10 and the light receiving optical system 20 with respect to the subject's eye 90. The anterior segment observation system 60 includes an observation two-dimensional sensor 61 (hereinafter, the sensor 61), an observation relay lens 62 (hereinafter, the lens 62), a first mirror 63, an observation diaphragm 64 (hereinafter, the diaphragm 64), a second mirror 65, and an illumination unit 66. The anterior segment observation system 60 further includes an alignment beam source 71 (hereinafter, the light source 71), an alignment diaphragm 72 (hereinafter, the diaphragm 72), and an alignment relay lens 73 (hereinafter, the lens 73) for use in alignment adjustment.

The sensor 61 is configured by a plurality of light receiving elements such as CCDs or CMOSs arranged side by side in a planar manner. The sensor 61 acquires an image of the anterior segment of the subject's eye 90. The image acquired by the sensor 61 is output to the control unit 50. The sensor 61 is positioned substantially conjugate with the pupil 92 of the subject's eye 90 (position indicated by (β) in the figure).

The lens 62 and the diaphragm 64 form an image of the anterior segment on the sensor 61. Between the lens 62 and the diaphragm 64, the first mirror 63 is disposed, which reflects light reflected on the anterior segment toward the sensor 61. The first mirror 63 transmits an alignment beam emitted from the light source 71.

The second mirror 65 is disposed between the objective lens 16 and the reflective mirror 32 on the optical axis of the light projecting optical system 10. The second mirror 65 reflects light reflected from the anterior segment toward the sensor 61, and reflects the alignment beam emitted from the light source 71 toward the subject's eye 90. Further, the second mirror 65 transmits the measuring beam emitted from the light source 11 and the reflected light reflected from the fundus 91.

The illumination unit 66 is a light source that projects an illumination beam used for imaging by the sensor 61 onto the anterior segment of the subject's eye 90. In the first embodiment, a plurality of the illumination units 66 may be disposed at positions to surround the optical axis of the light projecting optical system 10.

The light source 71 emits the alignment beam used for alignment adjustment. The light source 71 may emit an infrared ray having a wavelength (λ) of about 880 nm.

The diaphragm 72 and the lens 73 lead the alignment beam emitted from the light source 71 to the subject's eye 90. The diaphragm 72 has a through hole for narrowing and passing the alignment beam. The alignment beam passing through the diaphragm 72 causes specular reflection at a cornea of the subject's eye 90, and forms a point-like virtual image at substantially the same position as the pupil 92.

Now, a method of measuring and a method of calibrating eye refractive power of the subject's eye 90 by the apparatus 1 of the first embodiment will be described with reference to FIGS. 3 to 9D.

Figure 3:
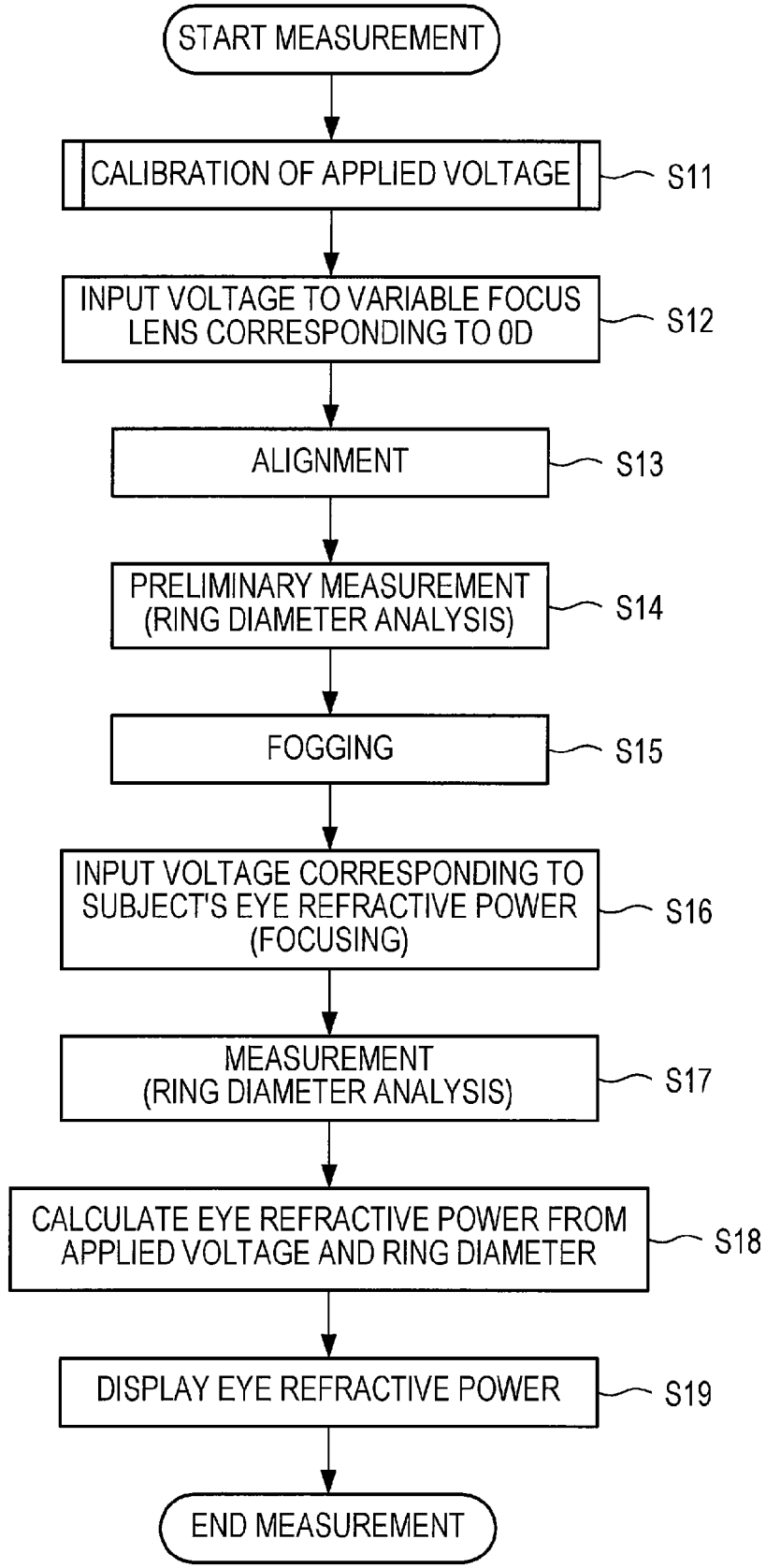
FIG. 3 is a flowchart illustrating a method of measuring eye refractive power according to the eye refractive power measuring apparatus.
Figure 4:
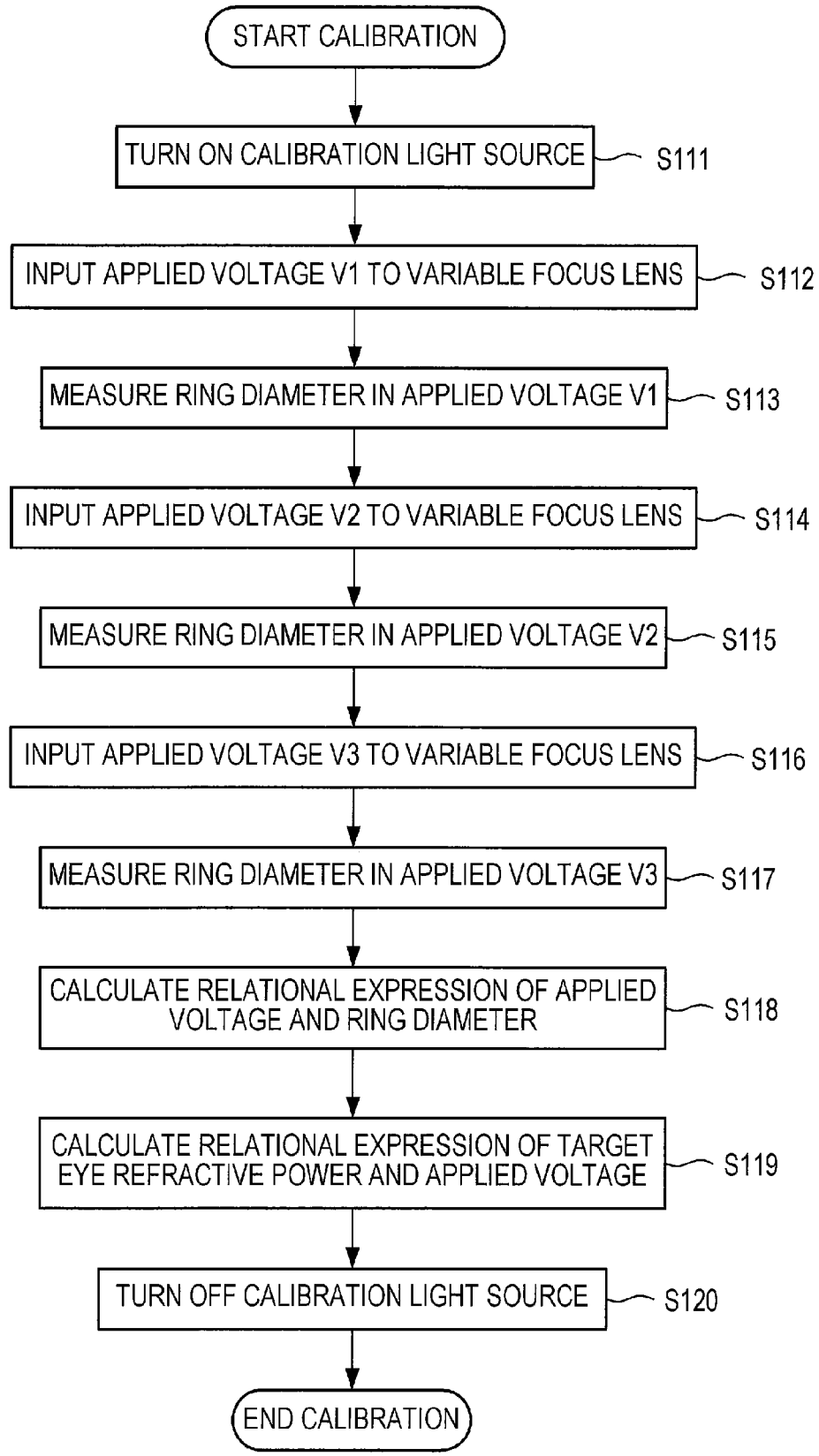
FIG. 4 is a flowchart illustrating a calibration method of a voltage applied to a variable focus lens.

When measurement of the eye refractive power by the apparatus 1 is started, the control unit 50 performs a calibration process of the applied voltage to be input to the lens 15 (S11), as shown in FIG. 3. In the calibration process of the applied voltage, a series of steps based on a flowchart shown in FIG. 4 are performed.

First, the control unit 50 executes a process of lighting the light source 31, in other words, a process of outputting a control signal that causes a calibration beam to be emitted (S111). At this time, if the light source 11 is lit, a process for outputting a control signal to turn off the light source 11 is also executed at the same time.

Thereafter, the focus control unit 51 of the control unit 50 executes a process of outputting an applied voltage V1 to the lens 15 (S112: an example of the acquiring step). The applied voltage V1 causes an image of the reflected light to be formed in focus on the sensor 21, when the subject's eye 90 is myopia. In this state, the control unit 50 executes a process for measuring a diameter of a ring (image of the calibration beam) formed on the sensor 21 (S113: an example of the acquiring step). Data of the measured diameter of the ring is stored in the storage unit 53.

Figure 5A:
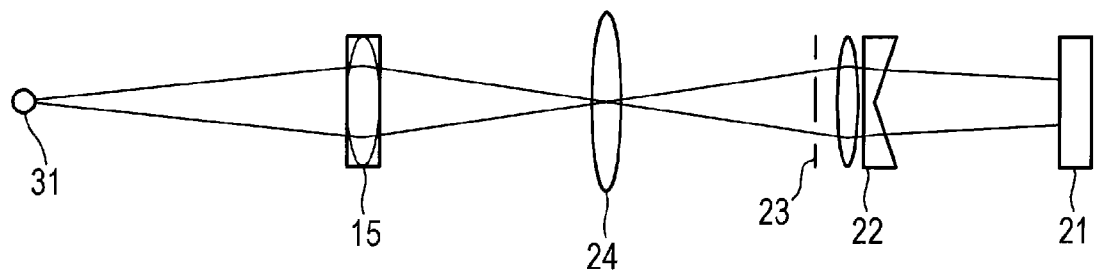
FIGS. 5A-5C are light beam schematic diagrams for a calibration beam in calibration for each applied voltage.

When the applied voltage V1 is applied, the focal position of the lens 15 is moved in a direction approaching the lens 15, as shown in FIG. 5A. The calibration beam emitted from the light source 31 reflects on the reflective mirror 32 (see FIG. 1) and is projected onto the ring diaphragm 23 through the lens 15 and the lens 24. The reflected light passing through a ring-shaped slit of the ring diaphragm 23 forms a ring-shaped image on the sensor 21 through the lens 22.

Figure 6A:
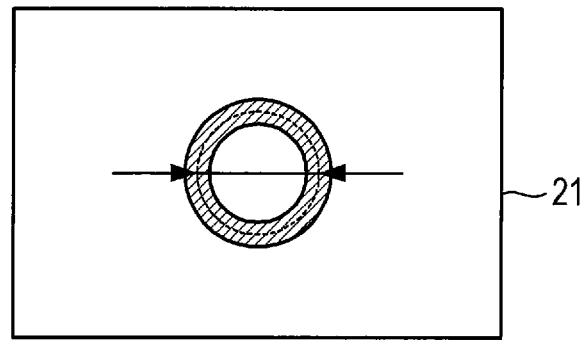
FIGS. 6A-6C are schematic diagrams illustrating change of a ring diameter, which is an image of the calibration beam in the calibration for each applied voltage.

Between the lens 22 and the sensor 21, the reflected light propagates along a conical surface whose diameter decreases toward the sensor 21. Thus, on the sensor 21, a ring-shaped image having a diameter as shown in FIG. 6A, for example a small diameter, is formed. The focus is out of the surface of the sensor 21, and an image having a large ring width (a blurred image) is formed.

To the control unit 50, a measurement signal of the ring-shaped image measured by the sensor 21 is input. In the arithmetic unit 52, a calculation for calculating the diameter of the ring-shaped image is performed based on the measurement signal. If the ring-shaped image ranges in size, the diameter is calculated using a center of gravity that is a position with the highest brightness. In FIG. 6A, a dotted line represents the position with the highest brightness, and an example of calculating a diameter of a circular ring represented by the dotted line is shown.

The focus control unit 51 of the control unit 50 executes a process of outputting an applied voltage V2 to the lens 15 (S114: an example of the acquiring step). The applied voltage V2 causes the image of the reflected light to be formed in focus on the sensor 21 when the subject's eye 90 is emmetropia. Then, the control unit 50 executes a process for measuring a diameter of a ring (image of the calibration beam) formed on the sensor 21 (S115: an example of the acquiring step). Data of the measured diameter of the ring is stored in the storage unit 53.

Figure 5B:
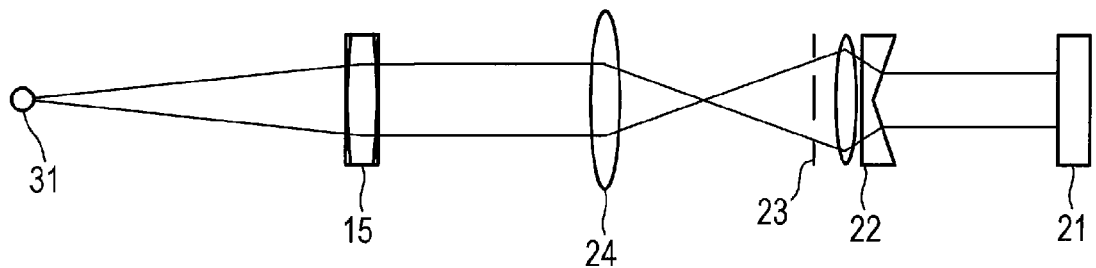
Figure 6B:
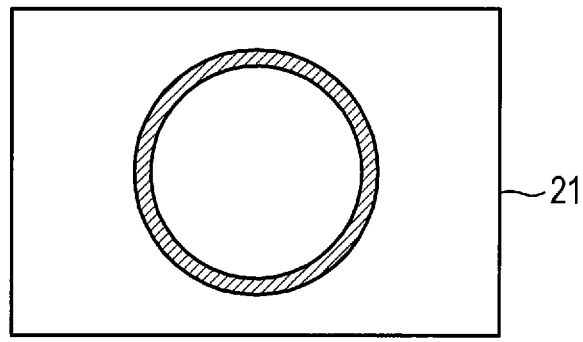

A state of the calibration beam at the time of applying the applied voltage V2 is as shown in FIG. 5B. Between the lens 22 and the sensor 21, the reflected light propagates along a cylindrical surface toward the sensor 21. The ring-shaped image formed on the sensor 21 is as shown in FIG. 6B, of which diameter is larger as compared with the case where the applied voltage V1 is applied. At this time, the surface of the sensor 21 is focused. An image having a small ring width (an image that is in focus) is formed.

The focus control unit 51 of the control unit 50 further executes a process for outputting an applied voltage V3 to the lens 15 (S116: an example of the acquiring step). The applied voltage V3 causes an image of the reflected light to be formed into an image having a large ring width (a blurred image) on the sensor 21, when the subject's eye 90 is hyperopia. The control unit 50 executes a process for measuring a diameter of the ring (image of the calibration beam) formed on the sensor 21 (S117: an example of the acquiring step). Data of the measured diameter of the ring is stored in the storage unit 53.

Figure 5C:
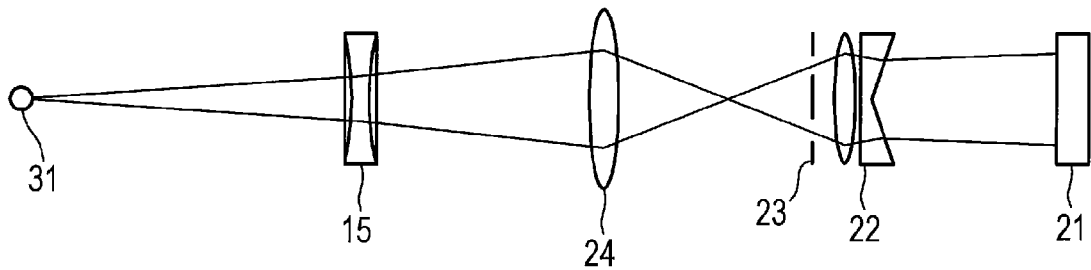
Figure 6C:
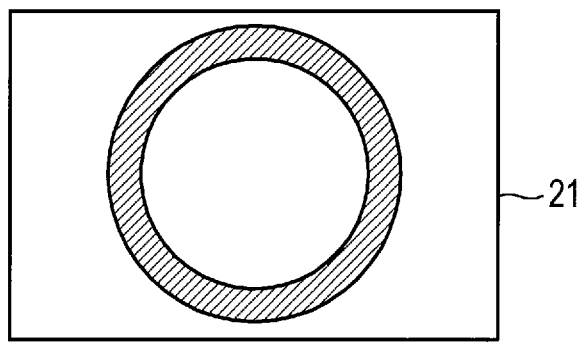
Figure 7:
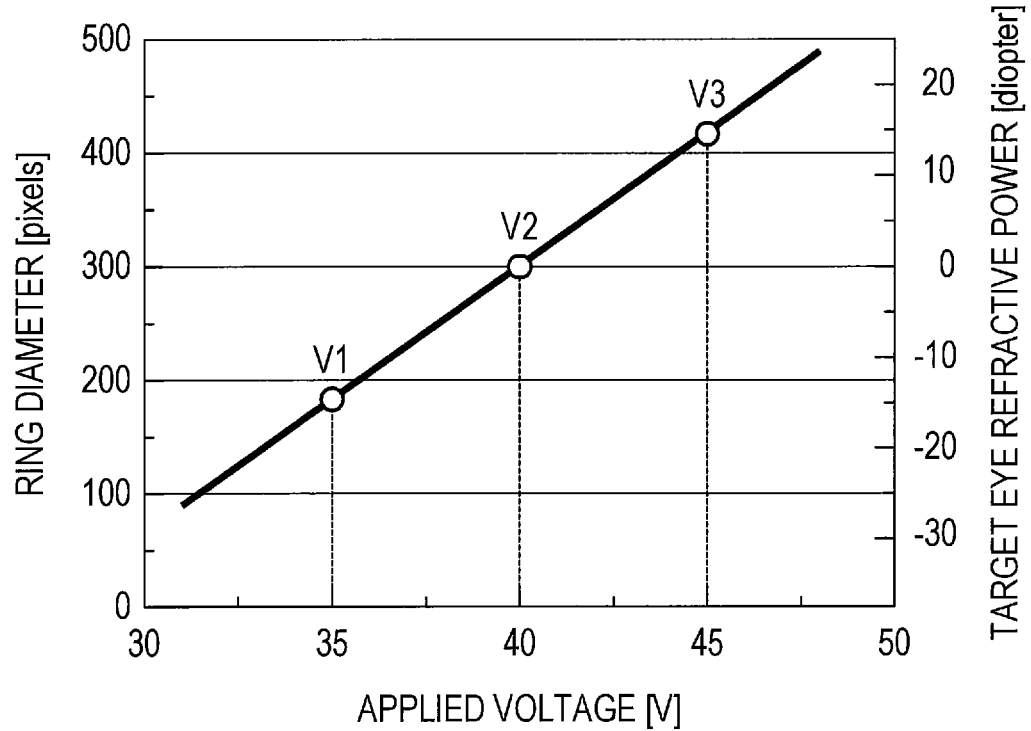
FIG. 7 is a graph showing a relation of the applied voltage, the ring diameter, and a target eye refractive power.

A state of the calibration beam at the time of applying the applied voltage V3 is as shown in FIG. 5C. Between the lens 22 and the sensor 21, the reflected light propagates along the conical surface spreading toward the sensor 21. The ring-shaped image formed on the sensor 21 is as shown in FIG. 6C, of which diameter is larger as compared with the case where the applied voltage V2 is applied. At this time, the focus is out of the surface of the sensor 21. The image having a wider ring is formed.

When measurement of the ring diameter in the applied voltages V1, V2, and V3 is finished, the arithmetic unit 52 executes a process of calculating a relation of the applied voltage and the ring diameter (S118: an example of the approximation step). Specifically, the arithmetic unit 52 executes a process for calculating an approximation formula of reading the ring diameter in the applied voltages V1, V2, and V3 stored in the storage unit 53 to approximate the relation of the applied voltage and the ring diameter. As a method for calculating the approximation formula, it is possible to use a known method such as a least square method. In the first embodiment, a case in which a relational expression is a linear function will be described, but the relational expression is not particularly limited and may be a function of higher order, such as a cubic function or a quadratic function.

When the relational expression of the applied voltage and the ring diameter is obtained, the arithmetic unit 52 executes a process of calculating a relational expression (correlation) of a target eye refractive power value (hereinafter, the target value) and the applied voltage (S119: an example of the correlation step). Specifically, the arithmetic unit 52 calculates a relational expression of the target value and the applied voltage based on data such as a correspondence table of the ring diameter and the target value stored in the storage unit 53 in advance, and the relational expression of the applied voltage and the ring diameter obtained in S118.

As the above correspondence data for the ring diameter and the target value, it is possible to illustrate data that is obtained when the apparatus 1 is produced and shipped. When the apparatus 1 is produced, the ring diameter to a simulated eye having a predetermined eye refractive power is measured using simulated eyes having various eye refractive power values. Thereby, the correspondence data of the ring diameter and the target value may be obtained.

When the relational expression of the target value and the applied voltage is obtained, the control unit 50 executes a process of outputting a control signal for turning off the light source 31 (S120). At this time, a process of outputting a control signal to turn on the light source 11 is also executed. Thus, the calibration process of the applied voltage is terminated.

Thereafter, as shown in the flowchart of FIG. 3, the focus control unit 51 of the control unit 50 executes a process of inputting an applied voltage corresponding to 0 D (0 diopter) to the lens 15 (S12). The applied voltage corresponding to 0 D is determined based on the relational expression of the target value and the applied voltage obtained by the calibration process described above. The 0 D means that the eye refractive power value of the subject's eye 90 is an eye refractive power value of an emmetropia eye.

Then, the control unit 50 executes a process of adjusting alignment (S13). The adjustment of alignment refers to position adjustment of a center of the subject's eye 90 (center of the pupil 92) and the optical axis of the light projecting optical system 10.

Figure 8:
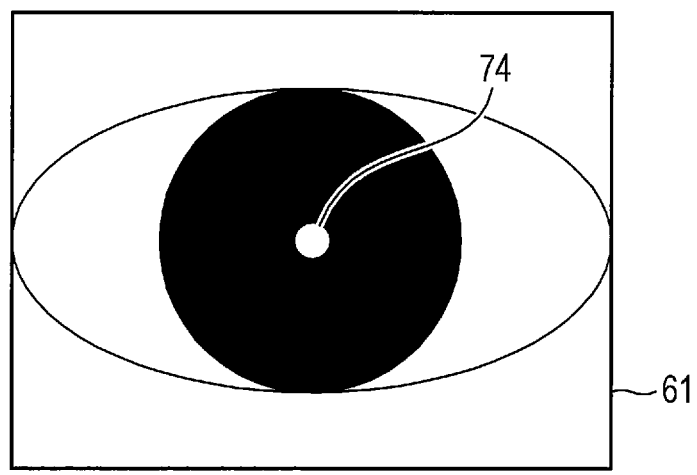
FIG. 8 is a schematic diagram for explaining an image acquired by an observation two-dimensional sensor.

On the sensor 61, as shown in FIG. 8, an image of the anterior segment of the subject's eye 90 is formed. At the center of the pupil 92 of the subject's eye 90, a bright spot 74 of the alignment beam emitted from the light source 71 can be observed. The control unit 50 performs a control of calculating a position of the bright spot 74 using a means like image processing, and moving the apparatus 1 in an X-axis direction and a Y-axis direction so as to match the position of the calculated bright spot 74 and the optical axis of the light projecting optical system 10.

In the image acquired by the sensor 61, the center of the image is the optical axis of the light projecting optical system 10. Thus, it can be expressed as that a control is executed to move the apparatus 1 in the X-axis direction and the Y-axis direction so that the bright spot 74 is to be positioned at the center of the image. After the optical axis is matched by moving in the X-axis direction and the Y-axis direction, the apparatus 1 is moved in a Z direction (longitudinal direction) so that a magnitude of the bright spot 74 is smaller. The alignment is then ended.

In the first embodiment, a case has been described in which alignment adjustment is performed automatically by the control unit 50. However, the adjustment method is not limited, and a person operating the apparatus 1 may perform the alignment adjustment manually.

After the alignment adjustment is completed, the control unit 50 performs a preliminary measurement of the eye refractive power (S14). When performing the preliminary measurement, the applied voltage corresponding to 0 D is applied to the lens 15, as described in S12.

Figure 9A:
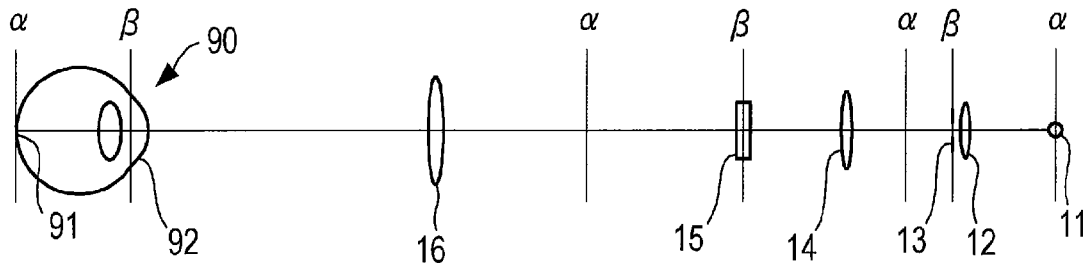
FIGS. 9A-9D are schematic ray diagrams for a light projecting optical system and a light receiving optical system of FIG. 1.
Figure 9B:
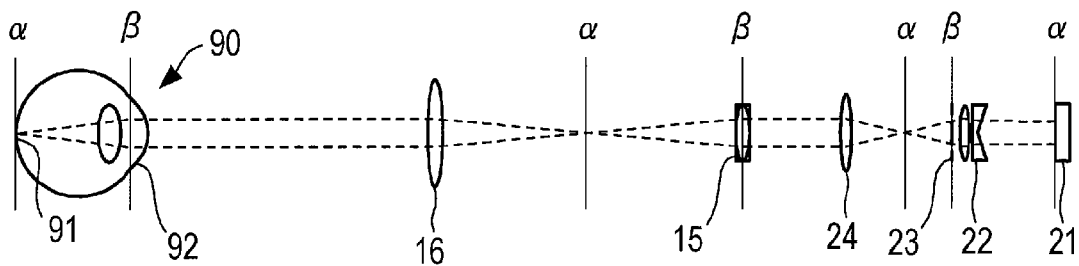
Figure 9C:
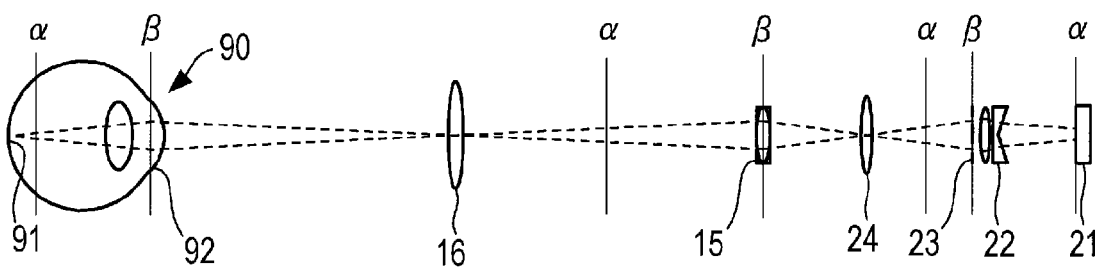

In the preliminary measurement, the measuring beam emitted from the light source 11 as shown in FIG. 9A is projected on the fundus 91 of the subject's eye 90. The projected measuring beam reflects on the fundus 91 to be a reflected light. As shown in FIG. 9B or 9C, the reflected light is imaged on the sensor 21 through the pupil 92, the objective lens 16, the lens 15, the lens 24, the ring diaphragm 23, and the lens 22.

FIG. 9B is a schematic ray diagram illustrating a case where the subject's eye 90 is emmetropia and the applied voltage corresponding to 0 D is applied to the lens 15. In this case, a ring as shown in FIG. 6B is imaged on the sensor 21. Further, FIG. 9C is a schematic ray diagram illustrating a case where the subject's eye 90 is myopia and the applied voltage corresponding to 0 D is applied to the lens 15. In this case, a ring as shown in FIG. 6A is imaged on the sensor 21.

To the control unit 50, a measurement signal of the ring-shaped image measured by the sensor 21 is input. In the arithmetic unit 52, a calculation for calculating a diameter of the ring-shaped image based on the measurement signal is executed. After calculating the diameter of the ring, the arithmetic unit 52 performs a calculation of calculating a preliminary eye refractive power of the subject's eye 90 based on the correspondence data of the ring diameter and the target value.

Then, the control unit 50 performs a control to apply fogging to the subject's eye 90 (S15). Specifically, based on the preliminary eye refractive power acquired in S14, the control unit 50 outputs to the moving unit 43 a control signal for moving the fixation target 41 to a position where the subject's eye 90 can focus on the fixation target 41, and causes the subject's eye 90 to gaze at the fixation target 41. Thereafter, a control signal for moving the fixation target 41 to a position where the subject's eye 90 cannot focus on the fixation target 41 is output to the moving unit 43. A control is performed that loosens the accommodation power in the subject's eye 90.

Then, the focus control unit 51 executes a process of applying to the lens 15 an applied voltage corresponding to the refractive power of the subject's eye 90 (S16). Specifically, based on the preliminary eye refractive power of the subject's eye 90 acquired in S14 and a relational expression of the target value and the applied voltage obtained in S119, an applied voltage corresponding to the preliminary eye refractive power is calculated, and the calculated applied voltage is applied to the lens 15.

Figure 9D:
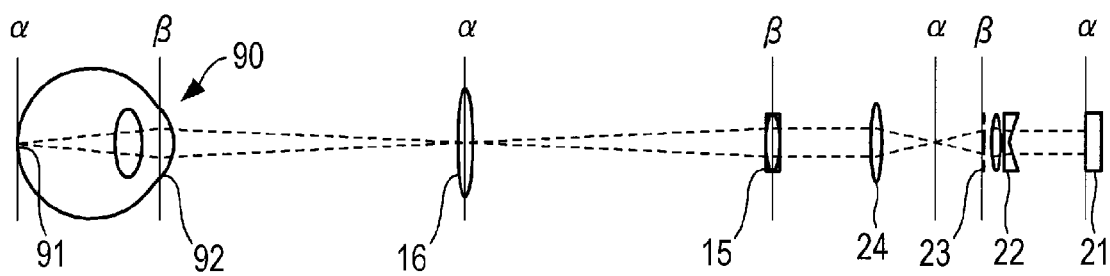

For example, if the preliminary eye refractive power is −15 D, an applied voltage corresponding to the −15 D is applied to the lens 15. A schematic ray diagram of the reflected light is as shown in FIG. 9D. At this time, the sensor 21 is focused, and the ring-shaped image as shown in FIG. 6B is formed.

Measurement of the ring diameter is performed in this state (S17). Specifically, a measurement signal of the ring-shaped image measured by the sensor 21 is input to the control unit 50. In the arithmetic unit 52, a calculation for calculating the diameter of the ring-shaped image is performed based on the measurement signal.

Further, the arithmetic unit 52, based on a relation of the applied voltage corresponding to −15 D applied to the lens 15 and the ring diameter measured in S17, executes a calculation for calculating the eye refractive power (S18: an example of the calibration step). Data showing a relation of the applied voltage, the ring diameter, and the eye refractive power is stored in the storage unit 53 in advance. The eye refractive power is calculated with reference to the data.

The process from S16 to S18 (measurement of the eye refractive power) may be once-off. On the other hand, when the position of the focal point of the reflected light to the sensor 21 is not within a predetermined range, the process from S16 to S18 may be repeated by changing the applied voltage. In other words, if the width of the ring-shaped image is not within a predetermined range, the process from S16 to S18 may be repeated until the width fits within the predetermined range. By causing the position of the focal point of the reflected light to the sensor 21 to fit within a predetermined range in this manner, accuracy of values of the eye refractive power to be calculated can be enhanced, as compared with the case where measurement of the eye refractive power is once-off.

Then, the arithmetic unit 52 executes a process for displaying the value of the calculated eye refractive power (S19). The value of refractive power to be displayed can be used as a reference when selecting a refractive power of a spectacle lens according to the subject's eye 90. Then, measurement of eye refractive power of the subject's eye 90 is completed.

According to the apparatus 1 configured as above, the relational expression of the applied voltage to be input to the lens 15 and the refractive power is acquired by using the calibration beam. Also, based on the control signal and the measured value of the sensor 21 when the measuring beam is projected, and the obtained relational expression, the eye refractive power of the subject's eye 90 is calculated. By using the relational expression in this way, it is possible to reduce errors in the refractive power of the subject's eye 90 to be calculated.

Specifically, at least change in characteristics of such as refractive power due to temperature changes and changes over time in the lens 15 is reflected on the relational expression obtained using the calibration beam. By correcting the eye refractive power of the subject's eye 90 obtained using the measuring beam based on the relational expression, errors that may be included in the eye refractive power can be reduced.

Further, as compared with the case of using a temperature control device in order to reduce errors due to temperature changes in the lens 15, the calibration optical system 30 does not require a large space for disposition, and can be disposed in the apparatus 1 at low price. Furthermore, even if the lens 15 is used that uses a relatively inexpensive material whose refractive power changes due to changes over time, spread of errors that may be included in the eye refractive power to be calculated can be prevented.

Even when a mechanism for moving the lens, etc. to move the focal position is used, use of the relational expression can suppress errors due to possible misalignment of the position of such as a lens before and after the movement.

By using the lens 15, as compared with the case of moving the lens to move the focal position, it becomes easy to suppress errors that may be included in the eye refractive power to be calculated. In the case of using a mechanism for moving the lens, etc., it is necessary to employ a moving mechanism that can suppress occurrence of misalignment between the optical axis of the lens and the optical axis of the light receiving optical system 20 due to the movement. In contrast, in the case of using the lens 15, it is possible to move the focal position without moving the position of the lens. Therefore, occurrence of misalignment of the optical axis due to the movement of the lens can be suppressed. It becomes easier to suppress errors due to such misalignment.

By providing the lens 15 in the light receiving optical system 20, the focal position of the reflected light imaged on the sensor 21 is controlled at least by the lens 15. Therefore, as compared with the case of controlling the focal position of the reflected light by the movement of the position of the lens, it is possible to reduce influence which the misalignment of the optical axis due to the movement of the lens has on the sensor 21. That is, it becomes easier to suppress errors that may be included in the eye refractive power to be calculated.

Furthermore, by providing the lens 15 in the area common to the light receiving optical system 20 and the light projecting optical system 10, it is possible to move the focal position of the reflected light, and the focal position of the measuring beam by the single lens 15. Therefore, as compared with the case of separately providing the lens 15 for moving the focal position of the reflected light and the lens 15 for moving the focal position of the measuring beam, it is possible to reduce the number of lens 15 to be used. It becomes easy to achieve downsizing of the apparatus 1 and reduction in manufacturing costs.

By disposing the lens 15 at the position substantially conjugate with the pupil 92 of the subject's eye 90, it is possible to prevent the reflected light from being focused on the position of the lens 15. Therefore, it becomes possible to move the focal position of the reflected light by the lens 15. As the position substantially conjugate with the pupil 92, it is possible to illustrate a range of about ±50 mm around a conjugate position of the pupil 92 of an emmetropia eye.

By disposing the light source 31 that emits the calibration beam at the position substantially conjugate with the fundus 91 of the subject's eye 90, as compared with the case where the light source 31 is not positioned substantially conjugate with the fundus 91, it is possible to calculate the relational expression that can further reduce errors that may be included in the eye refractive power to be calculated. That is, by using the calibration beam emitted from the light source 31 disposed at the position substantially conjugate with the fundus 91 when calculating the relational expression, as compared with the case where a calibration beam emitted from a position not substantially conjugate is used, it is possible to calculate the relational expression under conditions close to the case of measuring the reflected light from the fundus 91. As a result, it becomes easy to further suppress errors that may be included in the eye refractive power to be calculated.

In the calibration process of the applied voltage, by calculating the relational expression using at least the applied voltage V1 of the focal position corresponding to the case where the subject's eye 90 is myopia and the applied voltage V3 of the focal position corresponding to the case where the subject's eye 90 is hyperopia, it is possible to further suppress errors that may be included in the eye refractive power is calculated.

First Variation of First Embodiment

An apparatus according to a first variation of the first embodiment of the present invention will now be described with reference to FIG. 10. The basic configuration of the apparatus of the first variation is the same as that of the first embodiment. However, the position of the variable focus lens is different from that of the first embodiment. Thus, for the present first variation, the position of the variable focus lens will be described with reference to FIG. 10, and the description of the other components will not be repeated.

Figure 10:
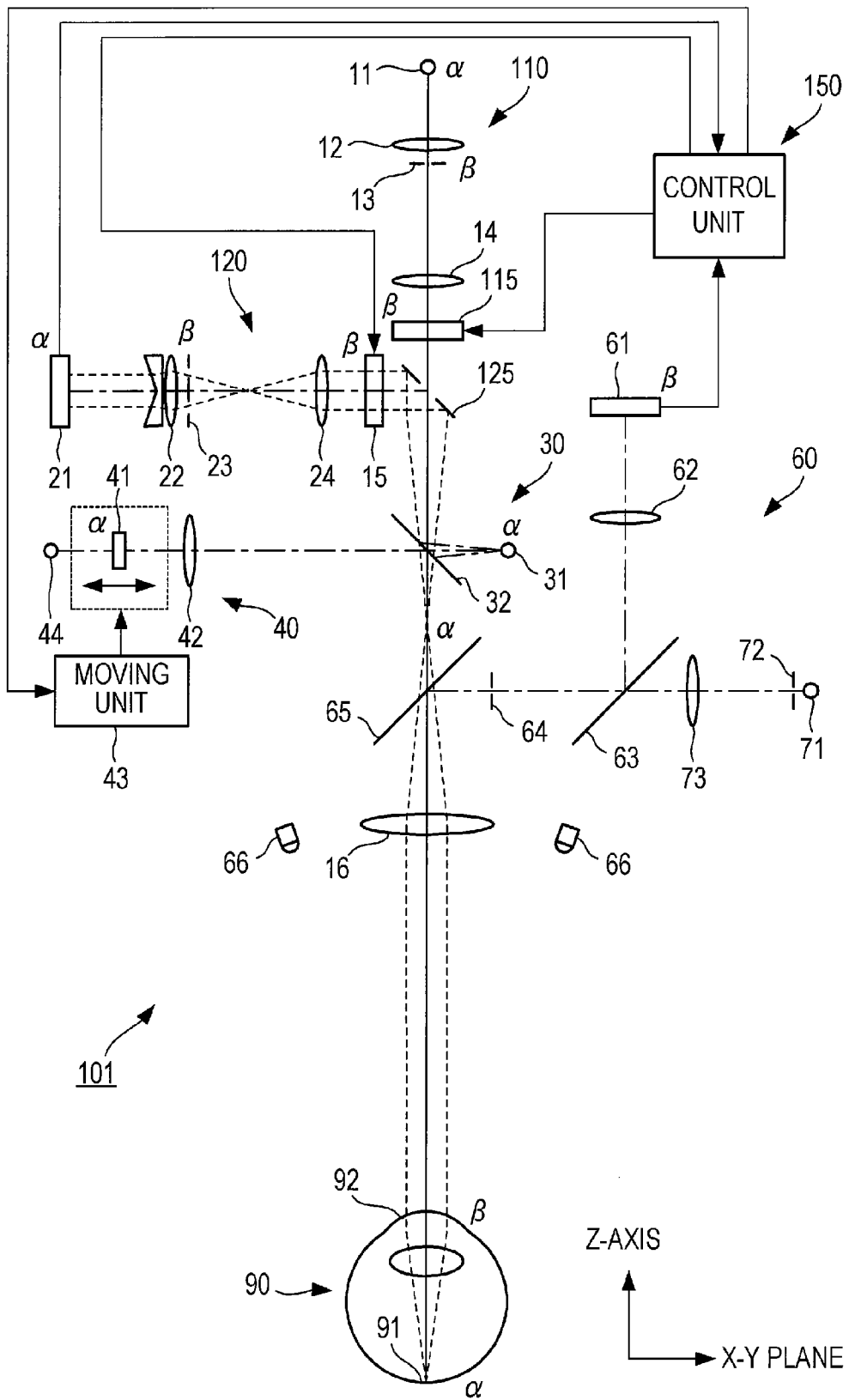
FIG. 10 is a schematic diagram illustrating the eye refractive power measuring apparatus according to a first variation of the first embodiment of the present invention.

An eye refractive power measuring apparatus 101 (hereinafter, the apparatus 101) according to the present first variation includes, as shown in FIG. 10, a light projecting optical system 110, a light receiving optical system 120, the calibration optical system 30, the fogging optical the system 40, and a control unit 150.

The light projecting optical system 110 projects a measuring beam used for measurement of eye refractive power toward the fundus 91 of the subject's eye 90. The light projecting optical system 110 includes the light source 11, the lens 12, the diaphragm 13, the lens 14, a variable focus lens (an example of the focusing unit) 115 (hereinafter, the lens 115), and the objective lens 16.

Unlike the first embodiment, the lens 115 provided in the light projecting optical system 110 of the first variation is not shared with the light receiving optical system 120. Other points such as a structure are the same as those of the lens 15 of the first embodiment. In other words, the lens 115 is different from the lens 15 of the first embodiment in that the lens 115 is disposed in a region that is in the light projecting optical system 110 and is independent of the light receiving optical system 120. The lens 115 is positioned between the lens 14 and the objective lens 16 and is substantially conjugate with the pupil 92 of the subject's eye 90.

The light receiving optical system 120 causes the sensor 21, described later, to receive the reflected light from the fundus 91. The light receiving optical system 120 includes the sensor 21, the lens 22, the ring diaphragm 23, the lens 24, the lens 15, a light receiving mirror 125 (hereinafter, the mirror 125), and the objective lens 16.

Unlike the first embodiment, the lens 15 provided in the light-receiving optical system 120 of the first variation is not shared with the light projecting optical system 110. Other points are the same as those in the first embodiment. In other words, the lens 15 is different from that of the first embodiment in that the lens 15 is disposed in a region that is in the light receiving optical system 120 and is independent of the light projecting optical system 110. The lens 15 is positioned between the lens 24 and the mirror 125 and is substantially conjugate with the pupil 92 of the subject's eye 90.

The mirror 125 is the same as the mirror 25 of the first embodiment, and is different only in the position disposed. Specifically, the mirror 125 is disposed between the lens 115 in the light projecting optical system 110 and the objective lens 16.

Similar to the control unit 50 of the first embodiment, the control unit 150 controls operation of the apparatus 101 and performs calculations required when calculating the eye refractive power of the subject's eye 90. The control unit 150 is different from the control unit 50 of the first embodiment in that the control unit 150 not only outputs an applied voltage to the lens 15, but also outputs an applied voltage to the lens 115.

A measuring method of eye refractive power of the subject's eye 90 by the apparatus 101 of the present first variation and a calibration method are the same as the measuring method and the calibration method in the first embodiment, and thus the description thereof is not repeated.

The apparatus 101 configured as above, by providing the lens 115 in the light projecting optical system 110 separately from the light-receiving optical system 120, can inhibit stray light generated by the measuring beam reflected on the lens 115 from entering the light receiving element 21.

Second Variation of the First Embodiment

An apparatus according to a second variation of the first embodiment of the present invention will now be described with reference to FIG. 11. The basic configuration of the apparatus of the second variation is the same as that of the first embodiment. However, the configuration of the fogging optical system is different from that of the first embodiment. Thus, for the present second variation, the fogging optical system will be described with reference to FIG. 11, and the description of the other components will not be repeated.

Figure 11:
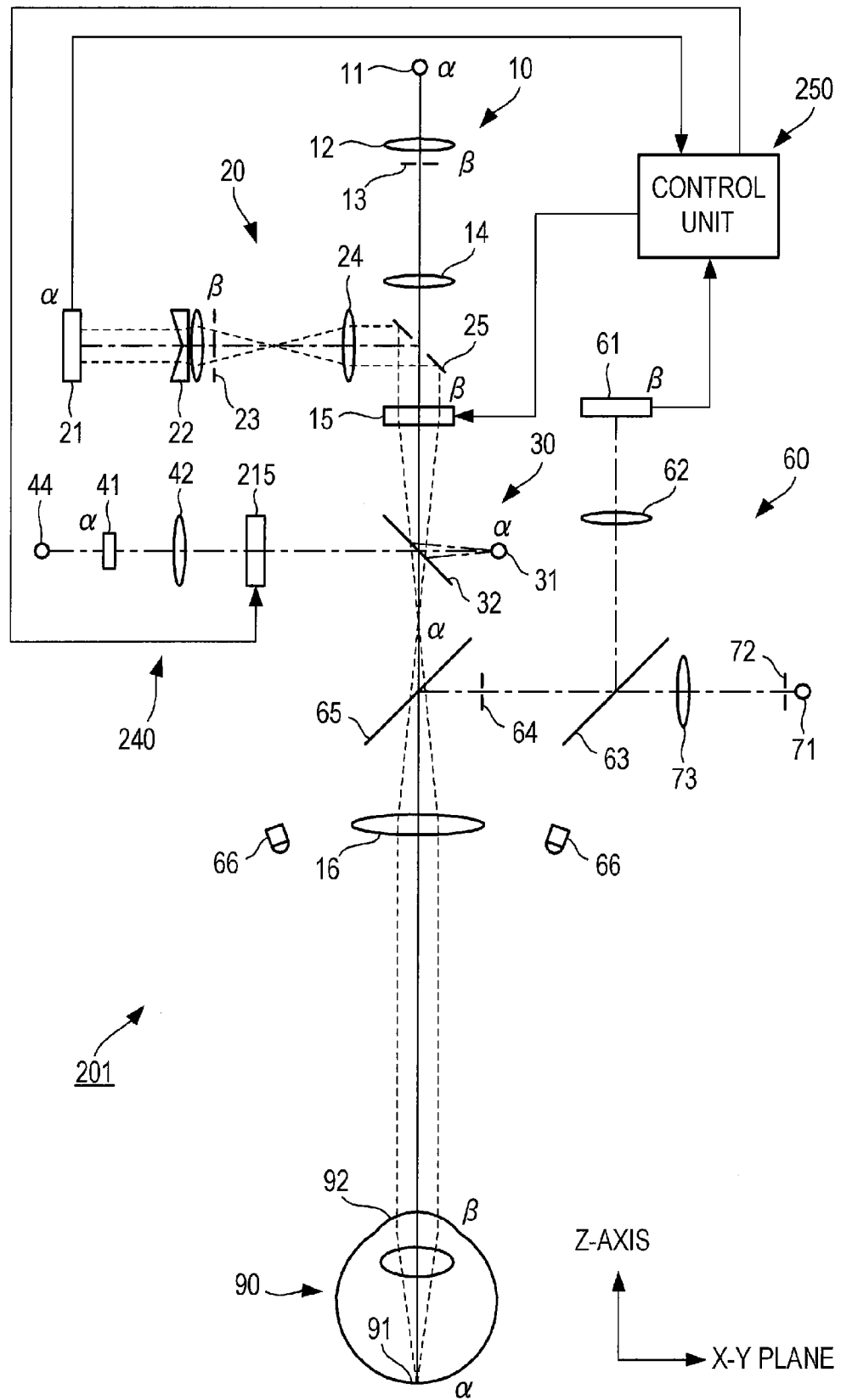
FIG. 11 is a schematic diagram illustrating the eye refractive power measuring apparatus according to a second variation of the first embodiment of the present invention.

An eye refractive power measuring apparatus 201 (hereinafter, apparatus 201) according to the present second variation includes, as shown in FIG. 11, the light projecting optical system 10, the light receiving optical system 20, the calibration optical system 30, a fogging optical system 240, and a control unit 250.

The fogging optical system 240 is used to bring a state in which accommodation power by a crystalline lens, etc. is not working, or a state in which influence on measurement of eye refractive power is small even if accommodation power is working, to the subject's eye 90. The fogging optical system 240 includes the visible light source 44, the fixation target 41, the lens 42, a variable focus lens 215 (hereinafter, the lens 215), and the reflective mirror 32.

The lens 215 provided in the fogging optical system 240 of the second variation is only different from the lens 15 of the first embodiment in that which of the optical systems the lens 215 is disposed in, and other points such as a structure is the same. The lens 215 is disposed between the lens 42 and the reflective mirror 32.

Similar to the control unit 50 of the first embodiment, the control unit 250 controls operation of the apparatus 201, and performs calculations required when calculating the eye refractive power of the subject's eye 90. The control unit 250 is different from the control unit 50 of the first embodiment only in that, instead of outputting a control signal to the moving unit 43 of the fogging optical system 240, the control unit 250 outputs an applied voltage to the lens 215.

A measuring method of eye refractive power of the subject's eye 90 by the apparatus 201 of the present second variation, and a calibration method are the same as the measuring method and the calibration method in the first embodiment, and thus the description thereof is not repeated.

By providing the lens 215 in the fogging optical system 240 and controlling the lens 215 based on the relational expression, it becomes easy for the apparatus 201 configured as above to bring the subject's eye 90 to a fogging state, as compared to the case without using the lens 215.

Second Embodiment

An apparatus according to a second embodiment of the present invention will now be described with reference to FIG. 12. The basic configuration of the apparatus of the second embodiment is the same as that of the first embodiment. However, configurations of the light projecting optical system and the light receiving optical system are different from those of the first embodiment. Thus, for the second embodiment, the configurations of the light projecting optical system and the light receiving optical system will be described with reference to FIG. 12, and the description of the other components will not be repeated.

Figure 12:
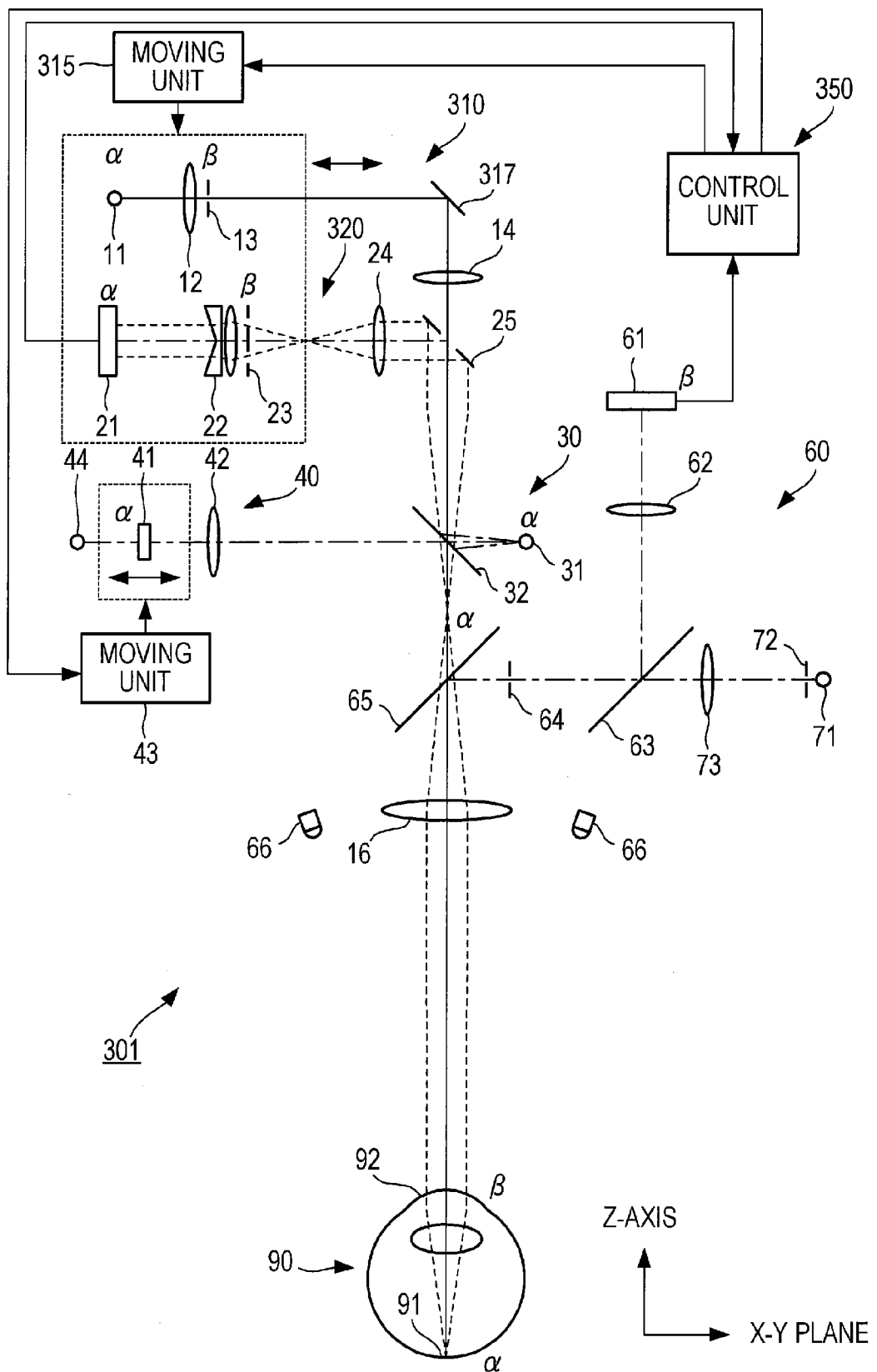
FIG. 12 is a schematic diagram illustrating the eye refractive power measuring apparatus according to a second embodiment of the present invention.

An eye refractive power measuring apparatus 301 (hereinafter, the apparatus 301) according to the second embodiment includes, as shown in FIG. 12, a light projecting optical system 310, a light receiving optical system 320, the calibration optical system 30, the fogging optical the system 40, and a control unit 350.

The light projecting optical system 310 projects a measuring beam used for a measurement of eye refractive power toward the fundus 91 of the subject's eye 90. The light projecting optical system 310 includes the light source 11, the lens 12, the diaphragm 13, the lens 14, a mirror 317, the objective lens 16, and a moving unit 315 (an example of the focusing unit).

The mirror 317 is disposed on an optical axis of the light projecting optical system 310. The optical axis from the light source 11 to the mirror 317 is parallel to the optical axis from the sensor 21 to the mirror 25 of the light receiving optical system 320.

The moving unit 315 is a driving mechanism that moves the light source 11, the lens 12, and the diaphragm 13 along the optical axis of the light projecting optical system 310 and moves the sensor 21, the lens 22, and the ring diaphragm 23 along the optical axis of the light receiving optical system 320. A control signal is input from the control unit 350 to the moving unit 315. According to the control signal, the moving unit 315 moves the light projecting optical system 310 and the light receiving optical system 320. As a configuration of the moving unit 315, it is possible to use a well-known linear drive mechanism, etc. Types of the drive mechanism are not particularly limited.

The light receiving optical system 320 causes the sensor 21 to receive the reflected light from the fundus 91. The light receiving optical system 320 includes the sensor 21, the lens 22, the ring diaphragm 23, the lens 24, the mirror 25, and the objective lens 16 shared with the light projecting optical system 310. The light receiving optical system 320 is different from the light receiving optical system 20 of the first embodiment in that the lens 15 is not provided. Further, the light receiving optical system 320 is different in that the sensor 21, the lens 22, and the ring diaphragm 23 are configured to be movable by the moving unit 315.

Similar to the control unit 50 of the first embodiment, the control unit 350 controls operation of the apparatus 301, and performs calculations required when calculating the eye refractive power of the subject's eye 90. The control unit 350 is different from the control unit 50 of the first embodiment only in that, instead of outputting an applied voltage to the lens 15, the control unit 350 outputs a control signal to the moving unit 315.

A measuring method of eye refractive power of the subject's eye 90 by the apparatus 301 of the second embodiment and a calibration method are the same as the measuring method and the calibration method in the first embodiment, and thus the description thereof is not repeated.

According to the apparatus 301 configured as above, errors due to such as misalignment of the position of such as the lens 22 and the lens 24 to be moved by the moving unit 315 (errors that may be included in the eye refractive power to be calculated) will be reduced.

Specifically, changes in the measured value of the sensor 21 due to misalignment, etc. of the position of such as the lens 22 and the lens 24 moved by the moving unit 315 are reflected in the relational expression obtained using the calibration beam. By correcting the eye refractive power of the subject's eye 90 obtained using the measuring beam based on the relational expression, it is possible to reduce errors in the eye refractive power.

In addition, in the case of the second embodiment, which uses the moving unit 315, use of the relational expression can suppress errors due to misalignment of the position of such as the lens 22 before and after the movement.

Reference Embodiment

Figure 13:
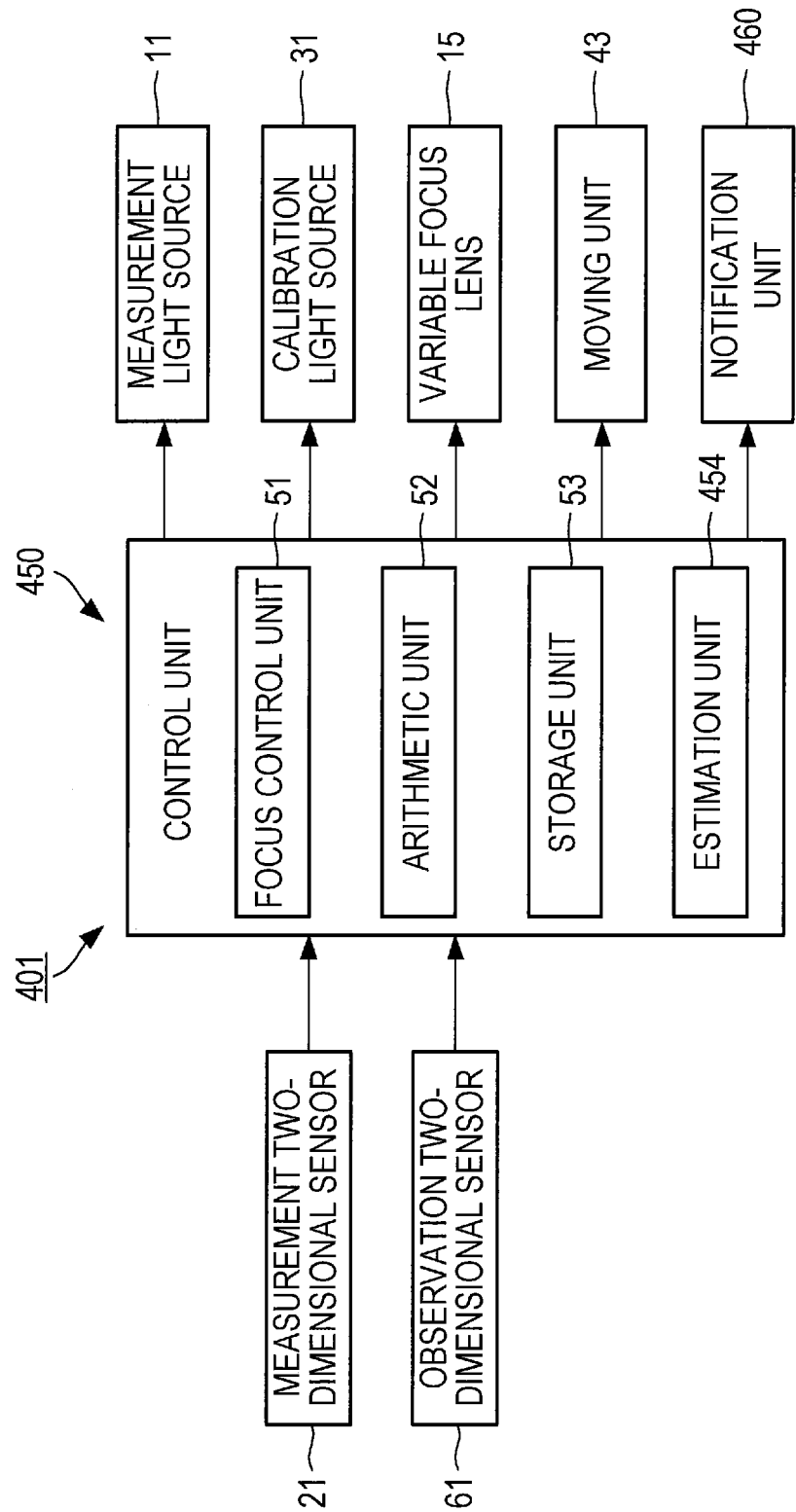
FIG. 13 is a block diagram of the control unit for explaining the eye refractive power measuring apparatus according to a reference embodiment of the present invention.

An apparatus according to a reference embodiment of the present invention will now be described with reference to FIGS. 13 and 14. The basic configuration of the apparatus of the present reference embodiment is the same as that of the first embodiment. However, the reference embodiment is different from the first embodiment in that the reference embodiment not only performs calibration of the apparatus, but also estimates causes of errors and encourages a customer to do maintenance depending on the causes of the errors.

For the reference embodiment, a portion related to estimation of causes of errors will be described with reference to FIG. 13. Because the other components are the same as those of the first embodiment, a description thereof is not repeated.

Similar to the control unit 50 of the first embodiment, a control unit 450 of an eye refractive power measuring apparatus 401 (hereinafter, apparatus 401) according to the reference embodiment controls operation of the apparatus 401 and also performs calculations required to calculate the eye refractive power of the subject's eye 90. In addition, the control unit 450 estimates causes of errors that may be included in the eye refractive power to be calculated by the apparatus 401.

The control unit 450 includes a microcomputer having a CPU (central processing unit), a ROM, a RAM, an input and output interface and so on. A control program stored in the ROM, etc. causes the CPU to function as the focus control unit 51, the arithmetic unit 52, and/or an estimation unit 454. The ROM or the RAM may correspond to an example of the storage unit 53.

The estimation unit 454 estimates the causes of errors that may be included in the eye refractive power to be calculated based on a relational expression obtained using the calibration beam. Examples of the causes of errors can be aging of the optical element such as the variable focus lens 51 and a relay lens, and misalignment of the position of the light projecting optical system 10 and/or the light receiving optical system 20.

A relational expression when the optical element is aging, and/or a relational expression when the position of the optical system is misaligned are calculated in advance, and these expressions are stored in the storage unit 53. By comparing the relational expression stored in the storage unit 53, and the relational expression that is obtained using the calibration beam, the estimation unit 454 can estimate the causes of errors that may be included in the eye refractive power to be calculated.

In comparison described above, if it is determined that the relational expression obtained using the calibration beam matches the relational expression stored in advance in the storage unit 53, the estimation unit 454 outputs a control signal that causes a notification unit 460 to display that maintenance is required. For example, the estimation unit 454 outputs a control signal that causes the notification unit 460 to display a message indicating that the optical element is aging, the optical element in question needs to be replaced, and the like.

By doing so, it is possible for the user to perform maintenance of the apparatus 401 only when needed. The user can efficiently maintain accuracy of measurement. Further, it is possible to suppress maintenance more than necessary to be performed in order to keep accuracy of measurement. Maintenance costs of the apparatus 401 can be saved.

Figure 14:
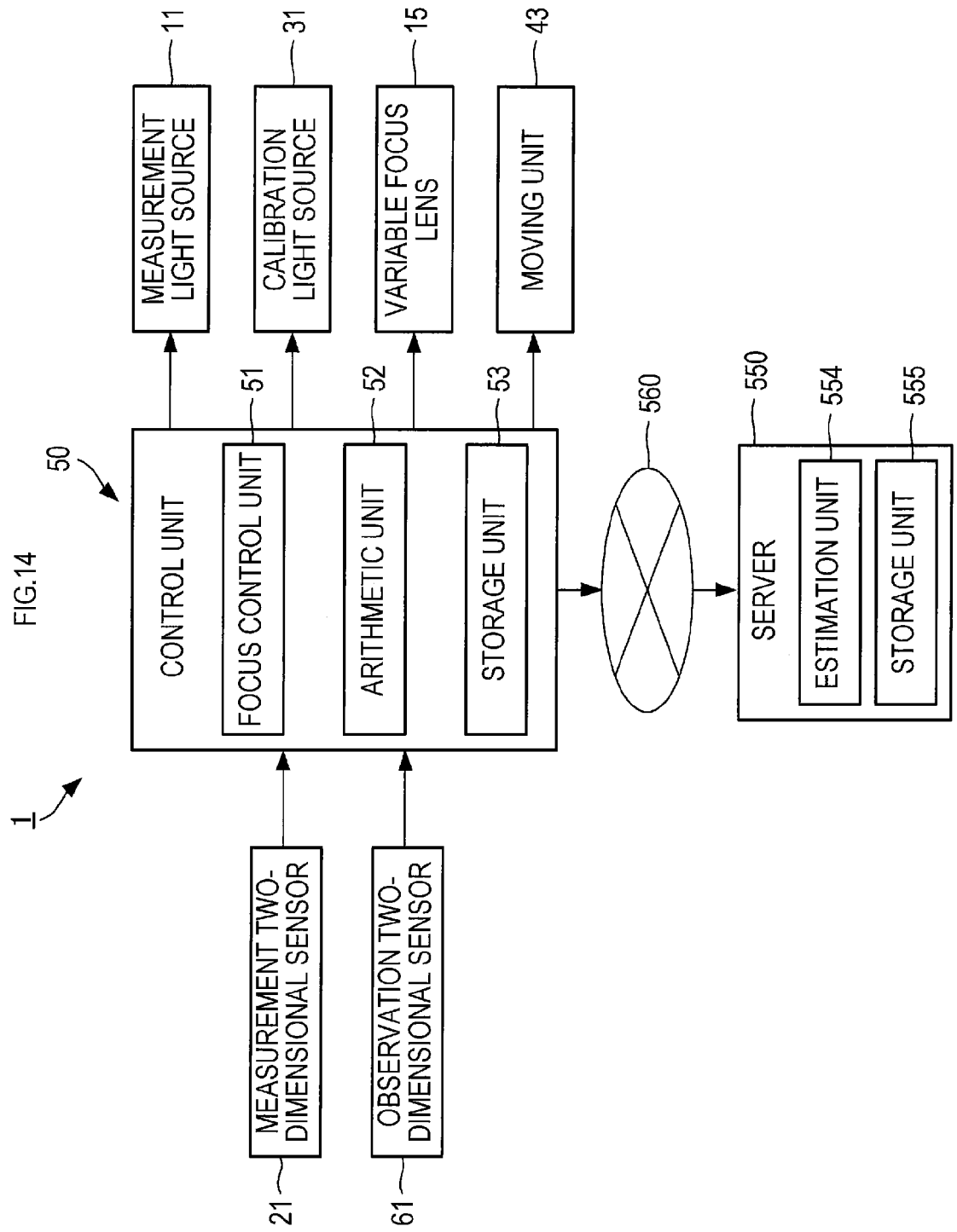
FIG. 14 is a block diagram of the control unit for explaining the eye refractive power measuring apparatus according to another reference embodiment of the present invention.
Figure 15:
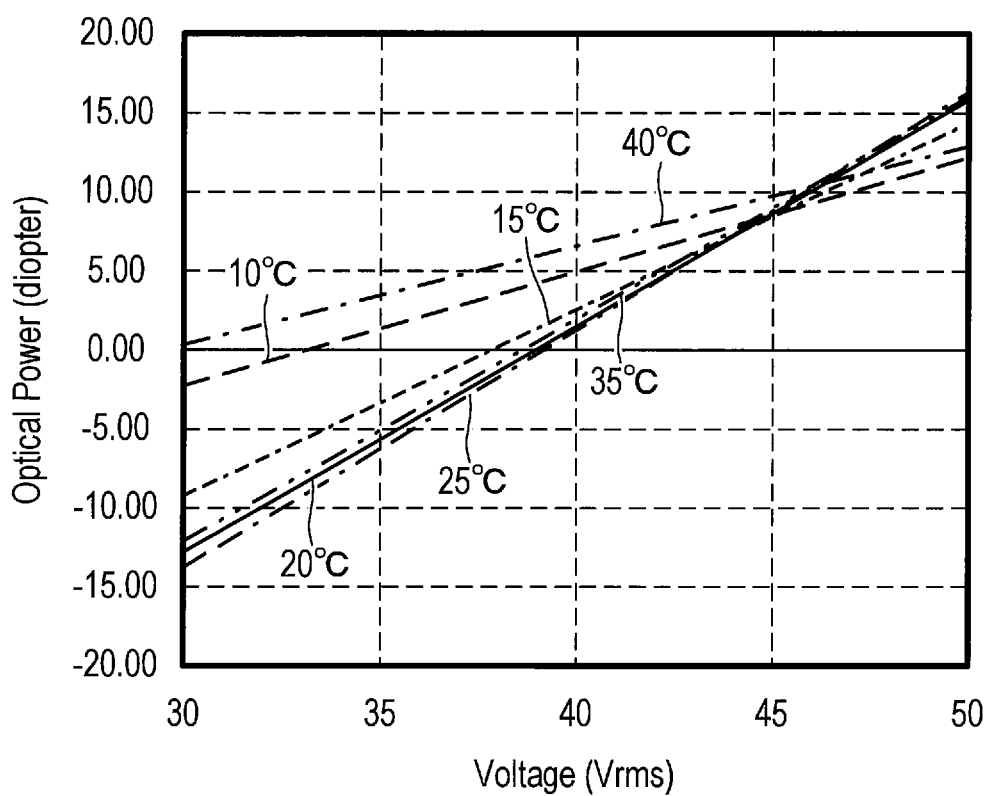
FIG. 15 is a graph showing an example of a relation of the applied voltage, the refractive power, and a temperature of a liquid lens (an example of a variable focus lens).

As in the embodiment described above, the apparatus 401 may be provided with the estimation unit 454 in the control unit 450, or, as shown in FIG. 14, may be provided with the estimation unit 554 and the storage unit 555 in a server 550 connected via the apparatus 1 of the first embodiment and an Internet 560. In this case, the server 550 may be disposed in a manufacturing company of the apparatus 1 or a company that performs maintenance, and may be connected to a plurality of the apparatus 1.

The estimation unit 554 estimates the causes of errors that may be included in the eye refractive power to be calculated based on the relational expression obtained using the calibration beam. The storage unit 555 may also store in advance a relational expression when the optical element has age deterioration. The storage unit 555 may also store in advance a relational expression when the position of the optical system is misaligned. If it is determined that the relational expression obtained using the calibration beam matches the relational expression stored in advance in the storage unit 555, the manufacturing company of the apparatus 1 notifies the user of the apparatus 1 that maintenance is required, and can dispatch a maintenance worker.

The technical scope of the present invention is not limited to the above embodiments, and various modifications can be made without departing from the scope of the present invention. For example, the present invention may be also applied to an embodiment that appropriately combines the above embodiments, and is not particularly limited.

[Supplementary Note 1]

An eye refractive power measuring apparatus comprising:

a light projecting optical system that projects a measuring beam for use in measurement of eye refractive power on a fundus of a subject's eye;

a light receiving optical system that causes a light receiving unit to receive reflected light from the fundus;

a focusing unit that forms an image of the reflected light on the light receiving unit by moving a focal position;

a calibration optical system that projects a calibration beam for use at least in calibration of the focusing unit, a focus control unit that outputs a control signal for controlling movement of the focal position to the focusing unit;

an acquisition unit that acquires a relation of the control signal obtained when the calibration beam is projected and a calibration value which is an output of the light receiving unit; and an estimation unit that estimates at least a state of the focusing unit, based on the acquired relation of the control signal and the calibration value.

[Supplementary Note 2]

The apparatus according to Supplementary note 1, further comprising a storage unit that stores in advance a correspondence between a relation of the control signal and a calibration value which is an output of the light receiving unit, and state of the focusing unit, wherein the estimation unit, based on the acquired relation of the control signal and the calibration value, and the correspondence stored in advance in the storage unit, estimates the state of the focusing unit.

[Supplementary Note 3]

An eye refractive power measuring system comprising:

an eye refractive power measuring apparatus comprising:

a light projecting optical system that projects a measuring beam for use in measurement of eye refractive power on a fundus of a subject's eye;

a light receiving optical system that causes a light receiving unit to receive reflected light from the fundus;

a focusing unit that forms an image of the reflected light on the light receiving unit by moving a focal position;

a calibration optical system that projects a calibration beam used at least for calibration of the focusing unit; and a focus control unit that outputs a control signal for controlling movement of the focal position to the focusing unit; and a monitoring apparatus comprising:

an acquisition unit that acquires a relation of the control signal obtained when the calibration beam is projected and a calibration value which is an output of the light receiving unit from the eye refractive power measuring apparatus; and an estimation unit that estimates at least a state of the eye refractive power measuring apparatus, based on the acquired relation of the control signal and the calibration value.

[Supplementary Note 4]

The system according to Supplementary note 3, wherein the monitoring apparatus further comprising a storage unit that stores in advance a correspondence between a relation of the control signal and a calibration value which is an output of the light receiving unit, and state of the focusing unit, and wherein the estimation unit, based on the relation of the acquired control signal and the calibration value, and the correspondence stored in advance in the storage unit, estimates the state of the focusing unit.

What is claimed is:

1. An eye refractive power measuring apparatus comprising:
   a light projecting optical system that projects a measuring beam for use in measurement of eye refractive power on a fundus of a subject's eye;
   a light receiving optical system that causes a light receiving unit to receive reflected light from the fundus;
   a focusing unit that forms an image of the reflected light on the light receiving unit by moving a focal position;
   a calibration optical system that projects a calibration beam for use in calibration of the focusing unit;
   a focus control unit that outputs to the focusing unit a control signal for controlling movement of the focal position; and
   an arithmetic unit that,
   based on a relation of the control signal obtained when the calibration beam is projected and a calibration value that is an output of the light receiving unit, and a correspondence relation of the calibration value and the eye refractive power obtained in advance, calculates a correlation of the control signal and the eye refractive power, and,
   based on the control signal obtained when the measuring beam is projected, a measured value that is an output of the light receiving unit, and the correlation, calculates the eye refractive power.

2. The apparatus according to claim 1 wherein
   the focusing unit is a variable focus lens in which focal position moves as refractive power changes in response to the input control signal.

3. The apparatus according to claim 2 wherein
   the variable focus lens is provided in the light receiving optical system, and moves the focal position of the reflected light that is imaged on the light receiving unit.

4. The apparatus according to claim 2 wherein
   the variable focus lens is provided in each of an area in the light receiving optical system independent of the light projecting optical system, and an area in the light projecting optical system independent of the light receiving optical system,
   the variable focus lens provided in the light receiving optical system moves the focal position of the reflected light imaged on the light receiving unit, and
   the variable focus lens provided in the light projecting optical system moves the focal position of the measuring beam projected on the fundus.

5. The apparatus according to claim 2 wherein
   the variable focus lens is provided in an area common to the light receiving optical system and the light projecting optical system, moves the focal position of the reflected light imaged on the light receiving unit, and moves the focal position of the measuring beam projected on the fundus.

6. The apparatus according to claim 2 further comprising
   a fogging optical system that presents a fixation target to the subject's eye, the fogging optical system having the variable focus lens, wherein
   the variable focus lens provided in the fogging optical system is controlled based on the control signal output by the focus control unit based on the correlation.

7. The apparatus according to claim 2 wherein
   the variable focus lens is arranged at a position substantially conjugate with a pupil of the subject's eye.

8. The apparatus according to claim 2 wherein
   a light source that emits the calibration beam in the calibration optical system is arranged at a position substantially conjugate with the fundus of the subject's eye, which is emmetropia.

9. A calibration method of the eye refractive power measuring apparatus according to claim 1, the method comprising:
   an acquisition step of projecting the calibration beam to the light receiving unit, outputting a plurality of the control signals having the different focal positions from the focus control unit to the focusing unit, and acquiring a calibration value, which is an output of the light receiving unit, every time the control signal is output;
   an approximation step of calculating an approximation formula representing a relation of the control signal and the corresponding calibration value;
   a correlation step of calculating a correlation of the control signal and the corresponding refractive power based on a correspondence relation of the calibration value, and the eye refractive power obtained in advance, and the approximation formula calculated in the approximation step; and
   a calibration step of calculating the eye refractive power based on the control signal obtained when the measuring beam is projected, a measured value that is an output of the light receiving unit, and the correlation.

10. The method according to claim 9 wherein
    in the obtaining step, the control signals having different focal positions output from the focus control unit include a signal of the focal position corresponding to a case where the subject's eye is myopia, and a signal of the focal position corresponding to a case where the subject's eye is hyperopia.

* * * * *